US007772461B2

(12) United States Patent
Fujiwara et al.

(10) Patent No.: US 7,772,461 B2
(45) Date of Patent: Aug. 10, 2010

(54) MOLYBDENUM TRANSPORTER GENE AND USE THEREOF

(75) Inventors: Toru Fujiwara, Tokyo (JP); Junpei Takano, Tokyo (JP); Hajime Tomatsu, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 227 days.

(21) Appl. No.: 11/908,537

(22) PCT Filed: Mar. 14, 2006

(86) PCT No.: PCT/JP2006/305061

§ 371 (c)(1),
(2), (4) Date: Oct. 23, 2007

(87) PCT Pub. No.: WO2006/098340

PCT Pub. Date: Sep. 21, 2006

(65) Prior Publication Data

US 2008/0216199 A1 Sep. 4, 2008

(30) Foreign Application Priority Data

Mar. 14, 2005 (JP) .............................. 2005-071991

(51) Int. Cl.
*C12N 15/09* (2006.01)
*C12N 15/82* (2006.01)
*A01H 5/00* (2006.01)

(52) U.S. Cl. ........................ 800/278; 800/298; 435/69.1

(58) Field of Classification Search ........................ None
See application file for complete search history.

(56) References Cited

U.S. PATENT DOCUMENTS 5,846,821 A * 12/1998 Guerinot et al. .......... 435/320.1
2004/0123343 A1  6/2004 La Rosa et al.

OTHER PUBLICATIONS

Rounsley et al. Accession No. AC006053; Deposited Mar. 11, 2002).*
Rounsley et al. Accession No. Q9SL95; Deposited May 1, 2000.*
Genoscope, "mth2-159D17RM1 BAC end, cultivar Jemalong A17 of *Medicago truncatula*, genomic survey sequence," GenBank Accession No. CR489095, Nov. 17, 2004.
Lin et al., "Hypothetical Protein, *Arabidopsis thaliana*," The Institute for Genomic Research, GenBank Accession No. AAD31368, Mar. 11, 2002.
Sato et al., "Barley EST Sequencing Project in NIG and Okayama University," GenBank Accession No. BJ458040, May 23, 2002.
Town et al., "putative sulfate transporter; 22471-23865, *Arabidopsis thaliana*," The Institute for Genomic Research, GenBank Accession No. AAG52436, Jan. 19, 2001.
Haas et al., "Full-Length Messenger RNA Sequences Greatly Improve Genome Annotation", Genome Biology, 3(6) pp. 1-12, 2002; Database Genbank Accession No. AY084878, Jun. 13, 2002.
Kikuchi et al., "Collection, Mapping, and Annotation of Over 28,000 cDNA Clones from japonica Rice," Science, vol. 301, No. 5631, pp. 376-379. Jul. 18, 2003; Database Genbank Accession No. AK106547, Jul. 19, 2003.
Kikuchi et al., "Collection, Mapping, and Annotation of Over 28,000 cDNA Clones from japonica Rice," Science, vol. 301, No. 5631, pp. 376-379, Jul. 18, 2003; Database Genbank Accession No. AK100928, Jul. 19, 2003.
*Brassica napus* mRNA for Putative Sulfate Transporter, Database Genbank Accession No. AJ311389, Dec. 16, 2002.
Xiao et al., "Cloning and Sequencing of cDNAs for Hypothetical Genes from Chromosome 2 of *Arabidopsis*," Plant Physiology, vol. 130, No. 4, pp. 2118-2128, Dec. 2002; Database Genbank Accession No. AY429372, Nov. 3, 2003.
Lin et al., "Sequence and Analysis of Chromosome 2 of the plant *Arabidopsis thaliana*," Nature, vol. 402, No. 6763, pp. 761-768, Dec. 16, 1999; Database Genpept Accession No. D84651, Nov. 25, 2002.
Tomatsu et al., "Identification of a Gene Controlling Molybdenum Content in *Arabidopsis thaliana*," The Japanese Society of Plant Physiologists Nenkai Oyobi Symposium Koen Yoshishu, PA179(506) Abstract, vol. 46, p. 231, 2005.
Self et al., "Molybdate Transport," Res. Microbiol., vol. 152, No. 3-4, pp. 311-321, 2001.
GqW76 Infected Wheat Roots with G. graminis Lambda Zap Express Library Triticum Aestivum/Gaeumannomyces Granminis mixed EST Library cDNA, mRNA sequence, Database Genbank Accession No. CF554492, Sep. 23, 2003.
MEST190-D07.T3 ISUM5-RN *Zea mays* cDNA clone MEST190-D07 3-, mRNA sequence, Database Genbank Accession No. BM336167, Jan. 16, 2002.
EST431131 GVSN *Medicago truncatula* cDNA clone pGVSN-16G14, mRNA sequnece, Database Genbank/EMBL/DDBJ/Geneseq Accession No. BE999408, Oct. 6, 2000.
N200651e rootphos (-) *Medicago truncatula* cDNA clone MHRP-19H3, mRNA sequence, Database Genbank Accession No. AW329416, Jan. 28, 2000.
Dudev et al., "Oxyanion Selectivity in Sulfate and Molybdate Transport Proteins: an ab Initio/CDM Study," J. Am. Chem. Soc., Aug. 25, 2004, 126(33):10296:305 (Abstract only).
Zahalak et al., "Molybdate Transport and Its Effect on Nitrogen Utilization in the Cyanobacterium *Anabaena variabilis* ATCC 29413," Molecular Microbiology, 2004, 51(2):539-549.
Buchner, P., "*Brassica napus* mRNA for putative sulfate transporter," GenBank Accession No. AJ311389, May 25, 2001.
GenBank Accession No. Q9SL95, Annotation for "At2g25680 *Arabidopsis thaliana* Q9SL95" Function Entry for Dec. 17, 2007.

* cited by examiner

*Primary Examiner*—Medina A Ibrahim
(74) *Attorney, Agent, or Firm*—Kenneth H. Sonnenfeld; King & Spalding LLP

(57) ABSTRACT

It is to provide a novel molybdenum ion transporter MoTR1 gene responsible for molybdenum transport for the first time in plants, enabling to promote effectively molybdenum absorption from the environment or molybdenum transport in vivo. By QTL analysis of *Arabidopsis thaliana* accessions Col-0 and Ler, it was found that QTL which dominates Mo concentration in leaves was present on the chromosome No: 2. In the present invention, the region in which the causal gene is present was limited to 172 kb, by a genetic analysis. In the region, the gene At2g25680 having a domain common to sulfate ion transporter, while its function is not revealed was present. Thus, knockout strains of 2 separate lines in which a foreign gene fragment (T-DNA) was introduced at At2g25680 were obtained, Mo concentration in leaves was measured, and MoTR1 gene was identified.

2 Claims, 6 Drawing Sheets (A) in the presence of molybdenum (B) in the absence of molybdenum

MOLYBDENUM TRANSPORTER GENE AND USE THEREOF

TECHNICAL FIELD

The present invention relates to a molybdenum transporter from *Arabidopsis thaliana, Oryza sativa*, rapeseed, *Hordeum vulgare, Triticum aestivum, Zea mays*, and *Medicago truncatula*, and genes thereof.

BACKGROUND ART

Molibdenum (Mo) is an essential element of plants (see for example, nonpatent document 1) and its lack induces symptoms including suppression of internodal growth, or morphological abnormality of leaves (see for example, nonpatent documents 2 and 3). Mo is a transition element, which is included in an enzyme catalyzing a plurality of oxidation/reduction reaction of plants, as an electron donor or receptor. Nitrate reductase which is responsible for an important reaction in nitrogen metabolic pathway, is one of the enzymes containing Mo (see for example, nonpatent document 4).

Mo binds with these enzymes in a form of Mo cofactor (Moco) bound to a pterin compound (see for example, nonpatent document 5). Moco is essential for nitrate reductase, and the activity of nitrate reductase is low in a mutated strain in which Moco content is reduced (see for example, nonpatent document 6). Mutated strains with a low nitrate reductase activity, show a perchlorate resistant and tungstate sensitive phenotypes (see for example, nonpatent document 7). By using these phenotypes as an index, mutated strains lacking enzymes necessary for biosynthesis of Moco were isolated, and the synthesis pathway of Moco has been clarified (see for example, nonpatent document 8). On the other hand, no mutated strain in which Moco content has been lowered because of reduction of Mo concentration in plants and causal genes thereof have been reported so far.

It is thought that plants absorb Mo mainly from soil in a form of $MoO_4^{2-}$, a bivalent negative ion (see for example, nonpatent document 9), and it is thought that a transporter intervenes in membrane penetration similarly to a general ion. In bacteria and archaea, an ABC-type (ATP-binding cassette type) Mo transporter has been identified (see for example, nonpatent document 10). However, Mo transporters have not been identified in plants.

It is known that when using $Na_2SO_4$ to grass farm containing a large amount of Mo, accumulation of Mo in pasture is suppressed (see for example, nonpatent document 11). It is thought that is because when $SO_4^{2-}$, a bivalent negative ion similar to $MoO_4^{2-}$, is also present in soil, Mo absorption of plants is competitively inhibited (see for example, nonpatent document 12), suggesting that $MoO_4^{2-}$ is transported from soil into plants by a mechanism similar to that of $SO_4^{2-}$.

Sulphur is a constitutive element of amino acids, and an essential element of plants. Plants incorporate sulfur in vivo by absorbing $SO_4^{2-}$, a bivalent negative ion, via a sulfate ion transporter (see for example, nonpatent document 13). By a sequence analysis of genomic DNA (see for example, nonpatent document 14), it was estimated that at least 14 sulfate ion transporters are present in *Arabidopsis thaliana*. The sulfate ion transporter family can be further classified into 5 groups according to its homology, and genes classified into groups 1 to 4 show the same characteristics in each group, for tissue-specific expression or intracellular localization (see for example, nonpatent document 15). On the other hand, the characteristics of the genes classified into group 5 have not been clarified (see for example, nonpatent document 16). A domain common in sulfate ion transporter family is present in the sequence of the genes of this group, while as a sequence as a whole, the homology with a sequence of genes belonging to other groups is low (see for example, nonpatent document 17). Further, it has not been reported that a translated product of genes belonging to group 5 has a sulfate ion transporter activity, and its function is unknown.

When comparing the element composition of *Arabidopsis thaliana* accessions Col-0 and Ler, Mo content in Col-0 is significantly high compared to that of Ler (see for example, nonpatent document 18).

[Patent document 1] Japanese Laid-Open patent application no. 2002-262872

[Nonpatent document 1] Amon, D. I. and Stout, P. R. (1939) The essentiality of certain elements in minute quantity for plants with special reference to copper. Plant Physiol. 14: 371/375

[Nonpatent document 2] Fido, R. J., Gundry, C. S., Hewitt, E. J. and Notton, B. A. (1977) Ultrastructural features of Molybdenum deficiency and whiptail of cauliflower leaves—effects of nitrogen-source and tungsten substitution for Molybdenum. Australian J. Plant Physiol. 4: 675-689

[Nonpatent document 3] Agarwala, S. C., Sharma, C. P., Farooq, S. and Chatterjee, C. (1978) Effect of Molybdenum deficiency on the growth and metabolism of corn plants raised in sand culture. Can. J. Bot. 56: 1905-1908

[Nonpatent document 4] Mendel, R. R. and Hansch, R. (2002) Molybdoenzymes and Molybdenum cofactor in plants. J. Exp. Bot. 53: 1689-1698

[Nonpatent document 5] Johnson, J. L., Hainline, B. E. and Rajagopalan, K. V. (1980) Characterization of the Molybdenum cofactor of sulfite oxidase, xanthine, oxidase, and nitrate reductase. Identification of a pteridine as a structural component. J. Biol. Chem. 255: 1783-1786

[Nonpatent document 6] Gabard, J., Pelsy, F., Marionpoll, A., Caboche, M., Saalbach, I., Grafe, R. and Muller, A. J. (1988) Genetic-analysis of nitrate reductase deficient mutants of *Nicotiana-plumbaginifolia*—evidence for 6 complementation groups among 70 classified Molybdenum cofactor deficient mutants. Mol. Gen. Genet. 21/3: 206-21/3

[Nonpatent document 7] LaBrie, S. T., Wilkinson, J. Q., Tsay, Y. F., Feldmann, K. A. and Crawford, N. M. (1992) Identification of two tungstate-sensitive Molybdenum cofactor mutants, chl2 and chl7, of *Arabidopsis thaliana*. Mol. Gen. Genet. 233:169-176

[Nonpatent document 8] Mendel, R. R. (1997) Molybdenum cofactor of higher plants: biosynthesis and Molecular biology. Planta 203: 399-405

[Nonpatent document 9] Gupta, U. C. and Lipsett, J. (1981) Molybdenum in soils, plants, and animals. Adv. Agron. 34: 73-115

[Nonpatent document 10] Self, W. T., Grunden, A. M., Hasona, A. and Shanmugam, K. T. (2001) Molybdate transport. Res. Microbiol. 152: 311/321

[Non patent document 11] Chatterjee, C., Nautiyal, N. and Agarwala, S. C. (1992) Excess sulphur partially alleviates copper deficiency effects in mustard. Soil Sci. Plant Nutr. 38: 57-64

[Nonpatent document 12] Pasricha, N. S., Nayyar, V. K., Randhawa, N. S. and Sinha, M. K. (1977) Influence of sulphur fertilization on suppression of Molybdenum uptake by berseem (*Trifolium alexandrinum* L.) and oats (*Avena sativa* L.) grown in a Molybdenum-toxic soil. Plant Soil 46: 245-250

[Nonpatent document 13] Smith, F. W., Ealing, P. M., Hawkesford, M. J. and Clarkson, D. T. (1995) Plant members of a family of sulfate transporters reveal functional subtypes. Proc. Natl. Acad. Sci. USA 92: 9373-9377

[Nonpatent document 14] The *Arabidopsis* Genome Initiative (2000) Analysis of the genome sequence of the flowering plant *Arabidopsis thaliana*. Nature 408: 796-815

[Nonpatent document 15] Hawkesford, M. J. (2000) Plant responses to sulfur deficiency and the genetic manipulation of sulfate transporters to improve S-utilization efficiency. J. Exp. Bot. 51: 1/31-1/38

[Nonpatent document 16] Hawkesford, M. J. (2003) Transporter gene families in plants: the sulphate transporter gene family. Redundancy or specialization Physiologia Plantarum 117: 155-163

[Non patent document 17] Buchner, P., Takahashi, H. and Hawkesford, M. J. (2004) Plant sulphate transporters: co-ordination of uptake, intracellular and long-distance transport. J. Exp. Bot. 55: 1765-1773

[Nonpatent document 18] Lahner, B., Gong, J., MahMoudian, M., Smith, E. L., Abid, K. B., Rogers, E. E., Guerinot, M. L., Harper, J. F., Ward, J. M., McIntyre, L., Schroeder, J. I. and Salt, D. E. (2003) Genomic scale profiling of nutrient and trace elements in *Arabidopsis thaliana*. Nat. Biotechnol. 21: 1215-1221

DISCLOSURE OF THE INVENTION

Object to be Solved by the Invention

Mo is an essential element of plants and its lack induces symptoms including suppression of internodal growth, or morphological abnormality of leaves. Mo is a transition element, which is included in an enzyme catalyzing a plurality of oxidation/reduction reaction of plants, as an electron donor or receptor. Nitrate reductase which is responsible for an important reaction of nitrogen metabolic pathway, is one of the enzymes containing Mo. It is thought that plants absorb Mo from soil mainly in a form of $MoO_4^{2-}$, a bivalent negative ion, and it is thought that a transporter intervenes in membrane penetration similarly to a general ion. In bacteria and archaea, an ABC-type Mo transporter has been identified. However, Mo transporters have not been identified in plants. It can be estimated that the elucidation of a molybdenum transport mechanism in plants at a molecular level, and the clarification of the main pathways or limiting factors of molybdenum transportation, will give knowledge to effective fertilizing method or breeding strategy. Further, the identification of genes associated with molybdenum transportation in plants is thought to be directly associated with generation of cultivars resistant to molybdenum deficiency/overexpression. The object of the present invention is to provide a novel gene responsible for molybdenum transportation in plants for the first time, enabling effective control of incorporation of molybdenum from environment or molybdenum transport in vivo.

Means to Solve the Object

The present inventors made a keen study to solve the above object, and identified MoTR1 gene encoding Mo transporter of *Arabidopsis thaliana*. This gene is semidominant, and determines Mo concentration in leaves. MoTR1 is a cell membrane protein, and is a transporter having an ability to concentrate Mo into a cell. Further, it was suggested that the Mo transporter is expressed in a tissue in which nitrate reduction is performed. It is explained in detail in the following.

(Identification of Genes)

The present inventors found out that QTL that dominates Mo concentration in leaves is present on the chromosome No: 2, by QTL analysis between *Arabidopsis thaliana* accessions Col-0 and Ler. In the present invention, the region in which a causal gene is present has been limited to the range of 172 kb, by a genetic analysis. In this region, the gene At2g25680 having a domain common with sulfate ion transporter, while its function being not analyzed, was present. As sulfur and Mo is absorbed into plants as $SO_4^{2-}$ and $MoO_4^{2-}$, it was thought that At2g25680 homologous to sulfate ion transporter may be associated with Mo absorption. Therefore, the present inventors obtained a knockout strain from 2 separate lines in which a foreign gene fragment (T-DNA) is inserted into At2g25680, and measured Mo concentration in leaves. The concentration was decreased in all of the mutated strains, to about ⅓ of a wild-type strain. This suggests that At2g25680 is a gene that determines Mo concentration in *Arabidopsis thaliana* leaves. Further, the Mo concentration in leaves of $F_1$ generation, obtained by crossing knockout stains of 2 separate lines was about ⅓ of that of a wild-type strain, and no phenotypes showing low Mo concentration was not complemented. Further, in $F_2$ generation obtained by self-pollination of $F_1$ generations, in which mutated strains were crossed with wild-types, Mo concentration in leaves of strains having the inserted gene genes as hetero, showed an intermediate level between a strain having the inserted gene as homo and a wild-type strain. These results support that the reduction of Mo concentration is caused by the mutation of At2g25680, and suggest that this mutation is self-dominant. From these results, since it has been confirmed that the cause of the reduction of Mo concentration in leaves of mutant strain was a mutation of At2g25680, this gene was designated as MoTR1.

(Intracellular Localization)

It was estimated that MoTR1 has 7 to 11 transmembrane regions. To investigate in which membrane of a cell a translated product is localized, a construct for expressing a fusion protein of MoTR1 and GFP (green Fluorescent protein) was prepared under control of cauliflower mosaic virus 35SRNA promoter and introduced into an onion epidermal cell. An observation with a laser confocal microscope showed that the fluorescence of the fusion protein was localized in the external marginal part of the cell. This result suggests that MoTR1 is a cell membrane protein.

(Mo Transport Activity)

In order to investigate the Mo transport activity of MoTR1, a construct for expressing MoTR1 in yeast was prepared and introduced into yeast. The transgenic strain and a wild-type strain were subcultured in a Mo-free medium, then transferred in a medium containing $1.7 \times 10^2$ nM of $MoO_4^{2-}$ and cultured by shaking for 30 min. By measuring Mo concentration in cells, the concentration in the transgenic strain was increased to 80 times or more than that of the wild-type strain. Further, Mo concentration in cells calculated by estimating the liquid content in cells from dried mass of cells, was higher than the Mo concentration in the medium. Therefore, MoTR1 may be a transporter having an ability to concentrate Mo against concentration gradient.

(Expression Tissues)

In order to investigate tissues in which MoTR1 express, β-glucuronidase (GUS) gene was linked to a promoter region approximately 2.9 kb upstream from the initiation codon of At2g25680 and transformed into *Arabidopsis thaliana*. In 16 independent lines of transgenic strains, GUS activity was confirmed in leaf stalk and outer edge of leaves in the aerial part. In root, GUS activity was confirmed in root apex, while no activity was observed in a region 1-6 mm from root apex. In an upper part thereof, GUS activity was observed in the pericycle, and in the region upper than where lateral root is observed, activity was observed in the cortex. The results were the same when GFP was used as a reporter in the same analysis. Expression pattern in root was similar to that of nitrate ion transporter AtNRT1.1 reported so far. There is a possibility that MoTR1 express in a tissue in which nitrate ion concentration is high, and provide Mo to nitrate reductase.

Next, by using the amino acid sequence of MoTR1 (456 amino acids) as a query, BLAST search of tblastn program on DDBJ website was performed. Molybdenum transporter genes from *Arabidopsis thaliana, Oryza sativa*, rapeseed, *Hordeum vulgare, Triticum aestivum, Zea mays*, and *Medicago Truncatula* were found out and molibudenum transport activity was confirmed for *Arabidopsis thaliana* and *Oryza sativa*.

The present invention was completed according to the above knowledge.

Specifically, the present invention relates to: (1) a DNA encoding a molybdenum transporter consisting of the amino acid sequence shown by SEQ ID No:2, 31, 33 or 35; (2) a DNA encoding a protein consisting of an amino acid sequence wherein one or a few amino acids are deleted, substituted or added in the amino acid sequence shown by SEQ ID No: 2, 31, 33 or 35, and having a molybdenum transporter activity; (3) a molybdenum transporter gene DNA consisting of the nucleotide (base) sequence shown by SEQ ID NO: 1, 30, 32 or 34 or its complementary sequence; (4) a DNA consisting of a nucleotide sequence wherein one or a few bases are deleted, substituted or added in the nucleotide sequence shown by SEQ ID NO: 1, 30, 32 or 34, and encoding a protein having a molybdenum transporter activity; (5) a DNA that hybridizes with the DNA according to (3) under stringent conditions, and encoding a protein having a molybdenum transporter activity; (6) a DNA encoding a protein comprising the amino acid sequence shown by SEQ ID No: 37, 39, 41, 43, 45, 47 or 49, and having a molybdenum transporter activity; (7) a DNA encoding a protein comprising an amino acid sequence wherein one or a few amino acids are deleted, substituted, or added in the amino acid sequence shown by SEQ ID NO: 37, 39, 41, 43, 45 or 47, and having a molybdenum transporter activity; (8) a DNA comprising the nucleotide sequence shown by SEQ ID No: 36, 38, 40, 42, 44, 46 or 48 or its complementary sequence, and encoding a protein having a molybdenum transporter activity; (9) a DNA comprising a nucleotide sequence wherein one or a few bases are deleted, substituted or added in the nucleotide sequence shown by SEQ ID No: 36, 38, 40, 42, 44, 46 or 48, and encoding a protein having a molybdenum transporter activity; (10) a DNA that hybridizes with a DNA consisting of the nucleotide sequence shown by SEQ ID No: 36, 38, 40, 42, 44, 46 or 48, or its complementary sequence under stringent conditions, and encoding a protein having a molybdenum transporter activity; (11) a molybdenum transporter consisting of the amino acid sequence shown by SEQ ID No: 2, 31, 33, or 35; (12) a protein consisting of an amino acid sequence wherein one or a few amino acids are deleted, substituted or added in the amino acid sequence shown by SEQ ID No: 2, 31, 33, or 35, and having a molybdenum transporter activity; (13) a protein comprising the amino acid sequence shown by SEQ ID No: 37, 39, 41, 43, 45, 47, or 49, and having a molybdenum transporter activity; (14) a protein comprising an amino acid sequence wherein one or a few amino acids are deleted, substituted or added in the amino acid sequence shown by SEQ ID No: 37, 39, 41, 43, 45, 47, or 49, and having a molybdenum transporter activity; (15) a recombinant vector comprising a DNA according to any one of (1) to (10), and capable of expressing a molybdenum transporter; (16) a transformant in which the recombinant vector according to (15) is introduced, and expressing a molybdenum transporter; (17) the transformant according to (16), wherein the transformant is yeast; (18) the transformant according to (16), wherein the transformant is a plant; (19) a molybdenum-fortified food or food material supplemented with the transformant according to anyone of (16) to (18) incorporated with molybdenum, or with a treated material thereof; (20) a molybdenum-fortified feed supplemented with the transformant according to any one of (16) to (18) incorporated with molybdenum, or with a treated material thereof; (21) a method for screening a material promoting or suppressing molybdenum transporter activity comprising the steps of allowing the transformant in which the recombinant vector according to (15) is introduced, and which expresses a molybdenum transporter to contact $MoO_4^{2-}$ in the presence of a test substance, and measuring/assessing the incorporation level of molybdenum into a cell; (22) the method for screening a material promoting or suppressing molybdenum transporter activity according to (21), wherein the transformant is yeast; (23) the method for screening a material promoting or suppressing molybdenum transporter activity according to (21), wherein the transformant is a plant.

Figure 1:
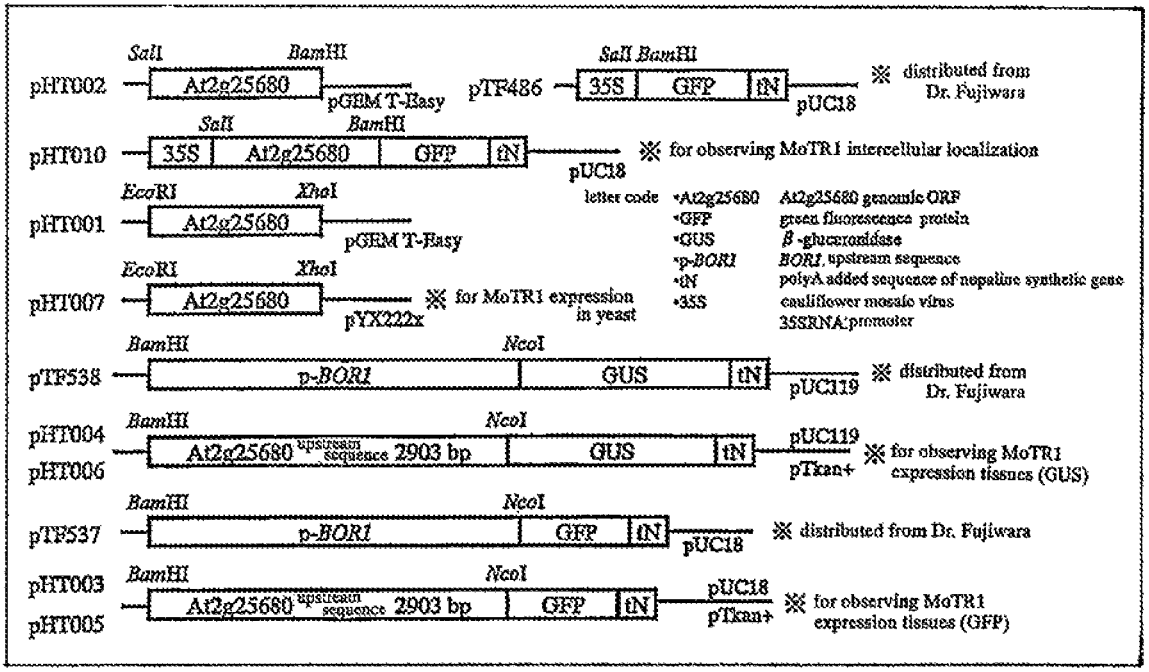
[FIG. 1]
It is a figure showing the measurement results of the present invention.

It is a graph showing Mo concentration in leaves of the back crossed-$F_2$ generation (SALK_118311×Col-0; $F_2$). $F_2$ seeds were obtained by self-pollination of $F_1$ generation strain, in which SALK_118311 are crossed with Col-0. The $F_2$ seeds, Col-0 and Ler, were inoculated on Rockwool, and cultured for 30 days by using MGRL water culture solution containing $1.7 \times 10^2$ nM of $MoO_4^{2-}$. Insertion of T-DNA into At2g25680 was confirmed by conducting PCR to $F_2$ generation, and the strains were classified into 3 strains: strains in which T-DNA is not inserted (wild-type); strains having the inserted gene as hetero (Hetero); strains having the inserted gene as homo (Homo). Mo concentration in leaves was measured for 4 plants in each strain, and the mean level is shown. Error bar shows the standard deviation. An alphabet is noted for each measurement level, the same alphabet shows that Mo concentration does not differ significantly in the same strain by Student's t test (P<0.05), and that when the letter is different, Mo concentration differs significantly.

[FIG. 5]

It is a figure showing intracellular localization of MoTR1:: GFP fusion protein. A construct for expressing a fusion protein of MoTR1 and GFP was prepared under control of cauliflower mosaic virus 35SRNA promoter and introduced into an onion epidermal cell. GFP fluorescence was observed with a laser confocal microscope. Scale bar shows 100 μm.

[FIG. 6]

It is a set of graphs showing Mo transport ability of MoTR1. A construct for expressing MoTR1 in yeast was prepared and introduced into yeast (*Saccaromyces cerevisiae*, BY4741). The transgenic strain and a wild-type strain were inoculated in a Mo-free medium and then subcultured. Cells during medium term of logarithmic growth phase were recovered by centrifugation, and re-suspended into a Mo-free medium (−Mo), or a medium in which $MoO_4^{2-}$ was added to a final concentration of $1.7 \times 10^2$ nM (+Mo), and cultured by shaking for 30 min. Cells after stirring were directly dried, to measure Mo concentration. Mo concentration of 4 strains which were subcultured from different colonies of each strain was measured, and the mean level of each strain was shown. Error bar shows the standard deviation. The lower graph is a graph in which the vertical axis scale of the above graph has been changed, showing the same data. Mo concentration of each strain differs significantly from other strain by Student's t test (P<0.05).

[FIG. 7]

It is a set of figures showing MoTR1-expression tissues. GUS gene was linked to a promoter region approximately 2903 bp upstream from the initiation codon of At2g25680 and transformed into *Arabidopsis thaliana*. GUS activity of the transformant 7 days after germination was observed with a light microscope ((B), (C), (D), (F), and (J)) or with a stereoscopic microscope ((H) and (I)). (A): GUS staining image of the transformant 7 days after germination. (B): Outer edge of cotyledon. (C) Stem of cotyledon. (D) Mature root (site 2 cm from root apex). (F): root apex. (H) Mature root (site 1 cm from root base). (I): mature root (site 2 cm from root apex). (J) Horizontal fragment of mature root (site 2 cm from root apex). Further, GFP gene was linked to a promoter region 2903 bp upstream of the initiation codon of At2g25680 and transformed into *Arabidopsis thaliana*. GFP fluorescence of transformation 7 days after germination was observed with a laser confocal microscope. (E): Mature root of the transformant 7 days after germination (site 2 cm from root apex; stained with propidium iodide). (G): Root apex. Scale bar shows 1 cm for (A), and 100 μm for others.

[FIG. 8]

It is a graph showing Km of a molybdenum transporter. Vercical axis indicates a reciprocal of molybdenum transport velocity (1/[Molybdenum velocity]), and horizontal axis indicates a reciprocal of Molybdenum concentration in the medium (1/[Molybdenum concentration in the medium]).

[FIG. 9]

It is a set of pictures showing the results of cultivating *Arabidopsis thaliana* (wild-type strain; mutated strain) for 3 weeks, under each condition. (A) shows those cultured in the presence of molybdenum, (B) shows those cultured in the absence of molybdenum.

[FIG. 10]

It is a graph showing Mo transport activity of *Oryza sativa* MoTR1, and MoTR2.

BEST MODE OF CARRYING OUT THE INVENTION

A DNA of the present invention is not particularly limited as long as it is a molybdenum transporter gene consisting of: a DNA encoding a protein consisting of the amino acid sequence shown by SEQ ID No: 2 (*Arabidopsis thaliana* MoTR1), SEQ ID No: 31 (*Arabidopsis thaliana* MoTR2), SEQ ID No: 33 (*Oryza sativa* MoTR1), SEQ ID No: 35 (*Oryza sativa* MoTR2); a DNA encoding a protein consisting of an amino acid sequence wherein one or a few amino acids are deleted, substituted, or added in the amino acid sequence shown by SEQ ID No: 2, 31, 33 or 35, and having a molybdenum (Mo) transporter activity; a molybdenum transporter gene DNA consisting of the nucleotide sequence shown by SEQ ID No: 1 (*Arabidopsis thaliana* MoTR1 gene), SEQ ID No: 30 (*Arabidopsis thaliana* MoTR2 gene), SEQ ID No: 32 (*Oryza sativa* MoTR1 gene), SEQ ID No: 34 (*Oryza sativa* MoTR2 gene), or its complementary sequence; a DNA consisting of a nucleotide sequence wherein one or a few bases are deleted, substituted, or added in the nucleotide sequence shown by SEQ ID No: 1, 30, 32, or 34, and encoding a protein having a molybdenum transporter activity, or a DNA that hybridizes with a DNA consisting of the nucleotide sequence shown by SEQ ID No: 1, 30, 32 or 34 under stringent conditions, and encoding a protein having a molybdenum transporter activity. Further, a DNA encoding a protein comprising the amino acid sequence shown by SEQ ID No:37 (rapeseed MoTR1), SEQ ID NO: 39 (*Hordeum vulgare* MoTR1), SEQ ID NO:41 (*Hordeum vulgare* MoTR2), SEQ ID NO: 43 (*Triticum aestivum* MoTR1), SEQ ID NO: 45 (*Zea mays* MoTR1), SEQ ID NO: 47 (*Medicago truncatula* MoTR1), SEQ ID NO: 49 (*Medicago truncatula* MoTR2), and having a molybdenum transporter activity; a DNA encoding a protein comprising an amino acid sequence wherein one or a few amino acids are deleted, substituted or added in the amino acid sequence shown by SEQ ID NO: 37, 39, 41, 43, 45, 47 or 49, and having a molybdenum transporter activity; a DNA comprising the nucleotide sequence shown by SEQ ID No:36 (rapeseed MoTR1 gene), SEQ ID NO: 38 (*Hordeum vulgare* MoTR1 gene), SEQ ID NO:40 (*Hordeum vulgare* MoTR2 gene), SEQ ID NO: 42 (*Triticum aestivum* MoTR1 gene), SEQ ID NO: 44 (*Zea mays* MoTR1 gene), SEQ ID NO: 46 (*Medicago truncatula* MoTR1 gene), SEQ ID NO: 48 (*Medicago truncatula* MoTR2 gene), or its complementary sequence, and encoding a protein having a molybdenum transporter activity; a DNA comprising a nucleotide sequence wherein one or a few bases are deleted, substituted, or added in the nucleotide sequence shown by SEQ ID No: 36, 38, 40, 42, 44, 46 or 48, and encoding a protein having a molybdenum transporter activity; or a DNA that hybridizes with a DNA consisting of the nucleotide sequence shown by SEQ ID No: 36, 38, 40, 42, 44, 46 or 48, or its complementary sequence under stringent conditions, and encoding a protein having a molybdenum transporter activity can be exemplified. Moreover, a protein of the present invention is not particularly limited as long as it is a molybdenum transporter consisting of the amino acid sequence shown by SEQ ID No: 2, 31, 33, or 35; or a protein consisting of an amino acid sequence wherein one or a few amino acids are added, substituted, or deleted in the amino acid sequence shown by SEQ ID No: 2, 31, 33, or 35, and having a molybdenum transporter activity; a protein comprising the amino acid sequence shown by SEQ ID No: 37, 39, 41, 43, 45, 47 or 49, and having a molybdenum transporter activity; or a molybdenum transporter protein consisting of a protein comprising an amino acid sequence wherein one or a few amino acids are deleted, substituted, or added in the amino acid sequence shown by 37, 39, 41, 43, 45, 47 or 49, and having a molybdenum transporter activity. The term "molybdenum transporter gene" herein mentioned relates to a gene associated with molybdenum transport, and the term "molybdenum transporter protein" relates to a protein associated with molybdenum transport.

The above-mentioned "protein having a molybdenum transporter activity" relates to a protein having an activity to transport molybdenum in vivo in the cells of yeast, plants, etc.

A molybdenum transporter gene can be exemplified by: *Arabidopsis thaliana* MoTR1 gene consisting of the nucleotide sequence shown by SEQ ID NO: 1; *Arabidopsis thaliana* MoTR2 gene consisting of the nucleotide sequence shown by SEQ ID NO: 30; *Oryza sativa* MoTR1 gene consisting of the nucleotide sequence shown by SEQ ID NO: 32; *Oryza sativa* MoTR2 gene consisting of the nucleotide sequence shown by SEQ ID NO: 34; rapeseed MoTR1 gene consisting of the nucleotide sequence shown by SEQ ID No: 36; *Hordeum vulgare* MoTR1 gene comprising the nucleotide sequence shown by SEQ ID No: 38; *Hordeum vulgare* MoTR2 gene comprising the nucleotide sequence shown by SEQ ID No: 40; *Triticum aestivum* MoTR1 gene comprising the nucleotide sequence shown by SEQ ID No: 42; *Zea mays* MoTR1 gene comprising the nucleotide sequence shown by SEQ ID No: 44; *Medicago truncatula* MoTR1 gene comprising the nucleotide sequence shown by SEQ ID No: 46; and *Medicago truncatula* MoTR2 gene comprising the nucleotide sequence shown by SEQ ID No: 48. Further, a molybdenum transporter protein can be exemplified by: *Arabidopsis thaliana* MoTR1 consisting of the amino acid sequence shown by SEQ ID NO: 2; *Arabidopsis thaliana* MoTR2 consisting of the amino acid sequence shown by SEQ ID NO: 31; *Oryza sativa* MoTR1 consisting of the amino acid sequence shown by SEQ ID NO: 33; *Oryza sativa* MoTR2 consisting of the amino acid sequence shown by SEQ ID NO: 35; rapeseed MoTR1 comprising of the amino acid sequence shown by SEQ ID No: 37; *Hordeum vulgare* MoTR1 comprising the amino acid sequence shown by SEQ ID No: 39; *Hordeum vulgare* MoTR2 comprising the amino acid sequence shown by SEQ ID No: 41; *Triticum aestivum* MoTR1 comprising the amino acid sequence shown by SEQ ID No: 43; *Zea mays* MoTR1 comprising the amino acid sequence shown by SEQ ID No: 45; *Medicago truncatula* MoTR1 comprising the amino acid sequence shown by SEQ ID No: 47; and *Medicago truncatula* MoTR2 comprising the amino acid sequence shown by SEQ ID No: 49.

"An amino acid sequence wherein one or a few amino acids are deleted, substituted or added" above mentioned relates to an amino acid sequence wherein, any number of amino acids, for example, 1 to 20, preferably 1 to 15, more preferably 1 to 10, further preferably 1 to 5 amino acids are deleted, substituted or added. Further, "a nucleotide sequence wherein one of a few bases are deleted, substituted or added" mentioned in the above, relates to a nucleotide sequence wherein, any number of bases, for example, 1 to 20, preferably 1 to 15, more preferably 1 to 10, further preferably 1 to 5 bases are deleted, substituted or added.

For example, a DNA consisting of a nucleotide sequence wherein one or a few bases are deleted, substituted or added (mutant DNA), can be prepared by any methods known to a person skilled in the art, such as chemosynthesis, genetic engineering method, or mutagenesis. Specifically, a mutant DNA can be obtained by introducing a mutation to a DNA consisting of the nucleotide sequence shown by SEQ ID No: 1, 30, 32, or 34, or a DNA comprising a nucleotide sequence shown by SEQ ID No: 36, 38, 40, 42, 44, 46 or 48, by using a method allowing the DNA to contact and react with an agent to be a mutagen, a method irradiating ultraviolet ray or a genetic engineering method. Site-specific mutagenesis, which is one of genetic engineering methods, is useful as it is a method that can introduce a specific mutation to a specific site. The method can be performed according to a method described in Molecular Cloning 2nd Edition: Current Protocols in Molecular Biology, Supplement 1-38, John Wiley & Sons (1987-1997). By expressing the mutant DNA with the use of an appropriate expression system, a protein consisting of an amino acid sequence wherein one or a few amino acids are deleted, substituted or added can be obtained.

The above-mentioned "nucleotide sequence that hybridizes under stringent conditions" relates to a nucleotide sequence that can be obtained by colony hybridization method, plaque hybridization method, or southern blotting hybridization method, with the use of nucleic acids such as DNA or RNA as a probe. Specifically, a DNA that can be identified by hybridizing at 65° C. in the presence of 0.7 to 1.0 M NaCl, with the use of a filter on which a DNA derived from a colony or a plaque, or a fragment thereof is immobilized, and by washing the filter with an approximately 0.1 to 2-fold SSC solution (one-fold concentration SSC solution is composed of 150 mM sodium chloride and 15 mM sodium citrate) under a condition of 65° C. can be exemplified. Hybridization can be performed according to a method described in Molecular Cloning: A Laboratory Manual, 2nd Ed., Cold Spring Harbor Laboratory, Cold Spring Harbor N.Y. 1989 (hereinafter referred to as "Molecular Cloning, 2nd Ed.")

In other words, "under stringent conditions" relates to a condition under which so-called specific hybrids are formed and nonspecific hybrids are not formed. Specifically, such conditions include a condition wherein DNAs with 50-70% or more homology are hybridized and DNAs with less homology are not hybridized, or a condition wherein hybridization occurs with a salt concentration corresponding to 1×SSC, 0.1% SDS or 0.1×SSC, 0.1% SDS at 65° C., which is a usual washing condition in southern hybridization. For example, as a DNA that can hybridize under stringent conditions can be exemplified by a DNA having above a certain homology with the nucleotide sequence of the DNA used as a probe. For example, a DNA having 60% or more of homology, preferably 70% or more, more preferably 80% or more, further preferably 90% or more, particularly preferably 95% or more, most preferably 98% or more, can be suitably exemplified.

A method for obtaining or preparing a gene of the present invention is not particularly limited, and it can be prepared by preparing a suitable probe or primer according to the nucleotide sequence information shown by SEQ ID No: 1, 30, 32, 36, 38, 40, 42, 44, 46 or 48, or the amino acid sequence information shown by SEQ ID No:2; screening a cDNA library in which the gene is estimated to be present by using the probe or primer; and isolating the intended gene, or by chemosynthesis according to common procedures.

Specifically, a gene of the present invention can be obtained by preparing a cDNA library according to common procedures from *Arabidopsis thaliana* from which the gene of the present invention has been isolated, and by selecting the intended clone from the library by using a suitable probe specific to the gene of the present invention. A source of the above cDNA can be exemplified by various cells or tissues of the above plants. Separation of all RNA from these cells or tissues, separation or purification of mRNA, acquisition of cDNA and its screening can all be performed according to common procedures. A method for screening a gene of the present invention from cDNA library can be exemplified by a method commonly used by a person skilled in the art, such as a method described in Molecular Cloning 2nd edition.

Further, the above-mentioned mutated gene or homologous gene of the present invention can be isolated by using a DNA fragment comprising a nucleotide sequence shown by a SEQ ID No: or a part thereof, and screening a homolog of the DNA from a different organism, etc. under suitable conditions. Alternatively, it can be prepared by a method for preparing a mutated DNA, described previously.

A method for searching a homologous gene can be exemplified by a method comprising performing BLAST search by tblastn targeting a nucleotide sequence registered to DDBJ, using the amino acid sequence of *Arabidopsis thaliana* MoTR1, *Arabidopsis thaliana* MoTR2, *Oryza sativa* MoTR1, *Oryza sativa* MoTR2, etc. as a query, and determining a homologous gene when the score of the obtained sequence is 100 or more. In that case, after aligning the amino acid sequence of the homologous gene and the amino acid sequence of MoTR1 by clustalW, the rate of amino acids conforming completely to the amino acids of the homologous gene can be determined as homology. Thus, rapeseed MoTR1 comprising the amino acid sequence shown by SEQ ID No:37; *Hordeum vulgare* MoTR1 comprising the amino acid sequence shown by SEQ ID No: 39; *Hordeum vulgare* MoTR2 comprising the amino acid sequence shown by SEQ ID No: 41; *Triticum aestivum* MoTR1 comprising the amino acid sequence shown by SEQ ID No: 43; *Zea mays* MoTR1 comprising the amino acid sequence shown by SEQ ID No:45; *Medicago truncatula* MoTR1 comprising the amino acid sequence shown by SEQ ID No: 47; *Medicago truncatula* MoTR2 comprising the amino acid sequence shown by SEQ ID No:49, etc. can be obtained.

A method for obtaining/preparing a protein of the present invention is not particularly limited, and the protein can be any one of: a naturally occurring protein, a chemosynthesized protein, or a recombinant protein prepared by a transgenic technology. When obtaining a naturally occurring protein, a protein of the present invention can be obtained by combining appropriately methods for isolating/purifying a protein from cells or tissues in which the protein is expressed. When preparing a protein by chemosynthesis, a protein of the present invention can be synthesized by chemosynthesis method such as F moc method (fluorenylmethyloxycarbonyl method) or tBoc method (t-butyloxycarbonyl method). Further, a protein of the present invention can be synthesized by using various peptide synthesizers commercially available. When preparing a protein by a transgenic technology, a protein of the present invention can be prepared by introducing a DNA consisting of a nucleotide sequence encoding the protein into a suitable expression system. Among these methods, preparation by transgenic technology enabling a preparation of a protein in a large amount by a relatively easy operation, is preferred.

For example, when preparing a protein of the present invention by a transgenic technology, known methods including ammonium sulfate or ethanol precipitation, acid extraction, anion or cation exchange chromatography, phosphocellulose chromatography, hydrophobic interaction chromatography, affinity chromatography, hydroxyapatite chromatography, and lectin chromatography, preferably high performance liquid chromatography is used. Particularly, for example, by using a column to which antibodies such as monoclonal antibodies against a protein of the present invention are bound, or a column to which a substance having affinity to the peptide tag when a normal peptide tag is added to a protein of the present invention, as a column to be used for affinity chromatography, a purified substance of these proteins can be obtained. Further, when a protein of the present invention is expressed on a cell membrane, a purified sample can be obtained by performing the above-mentioned purification treatment after allowing a cell membrane degrading enzyme to act.

Moreover, a protein consisting of an amino acid sequence wherein one or a few amino acids are added, substituted or deleted in the amino acid sequence shown by SEQ ID No: 2, 31, 33, or 35, or SEQ ID No: 37, 39, 41, 43, 45, 47 or 49, or a protein consisting of an amino acid sequence having 60% or more homology with the amino acid sequence shown by SEQ ID No:2, can be appropriately prepared or obtained by a person skilled in the art, according to the nucleotide sequence information shown by SEQ ID No: 1 showing an example of a nucleotide sequence encoding the amino acid sequence shown by SEQ ID No: 2. For example, it can be isolated by screening a homolog of a DNA comprising the nucleotide sequence shown by SEQ ID No:1 or a part thereof, under appropriate conditions from organisms other than *Arabidopsis thaliana* by using the DNA as a probe. By cloning the full-length DNA of the homolog DNA, introducing it into an expression vector to express it in an appropriate host cell, a protein encoded by the homolog DNA can be generated.

A recombinant vector of the present invention is not particularly limited as long as it is a recombinant vector comprising the above-mentioned genetic DNA of the present invention, and being able to express a molybdenum transporter. A recombinant vector of the present invention can be constructed by integrating appropriately a gene of the present invention into an expression vector. For example, a construct wherein an ORF cDNA from which the non-translated region of both 5' and 3' ends of a gene of the present invention is excluded, is bound to downstream of a cauliflower mosaic virus (CaMV) 35S promoter [Mol. Gen. Genet (1990) 220, 389-392], Triosephosphate Isomerase promoter, MoTR1 (At2g25680) promoter, etc. can be exemplified. As an expression vector, one being able to self-replicate in a host cell, or one being able to be integrated into a chromosome of a host cell is preferred. Further, an expression vector comprising a regulatory sequence such as promoter, enhancer, and terminator in a site where a gene of the present invention can be expressed, can be suitably used. As an expression vector, expression vector for yeast, expression vector for plant cells, expression vector for bacteria, and expression vector for animal cells can be used, while a recombinant vector using an expression vector for yeast, or an expression vector for plant cells is preferred.

As an expression vector for yeast, pGEM-T Easy Vector (Promega), pYES2 (Invitrogen), YEp13 (ATCC37115) YEp24 (ATCC37051), Ycp50 (ATCC37419), pHS19, and pHS15 can be exemplified. As a promoter for yeast, promoters including PHO5 promoter, PGKpromoter, GAPpromoter, ADHpromoter, GAL1 promoter, GAL10 promoter, heat shock protein promoter, MFα1 promoter, CUP1 promoter can be specifically exemplified.

As an expression vector for plant cells, plasmids including Ti plasmid (Tumor inducing plasmid), pSPORT1, pT7Blue-T vector, pIG121-Hm [Plant Cell Report, 15, 809-814 (1995)], pBI121 [EMBO J. 6, 3901-3907 (1987)], or plant viral vectors including tobacco mosaic virus, cauliflower mosaic virus, Geminivirus can be exemplified. As a promoter for plant cells, cauliflower mosaic virus 35S promoter [Mol. Gen. Gent (1990) 220, 389-392], and ribulose bisphosphate carboxylase small subunit promoter can be exemplified. As a terminator, a terminator of Nopalin synthase gene can be exemplified.

A transformant of the present invention is not particularly limited as long as it is a transformant in which the above-mentioned recombinant vector of the present invention is introduced, and expressing a molybdenum transporter. Examples include a transgenic yeast, transgenic plant (cell, tissue, individual), transgenic bacteria, transgenic animal (cell, tissue, individual), while transgenic yeast or transgenic plant (cell, tissue, individual) is preferred.

A host yeast to be used for preparing transgenic yeast, can be exemplified by *Saccharomyces cerevisae, Schizosaccharomyces pombe, Kluyveromyces lactis, Trichosporon pullulans*, and *Schwanniomyces alluvius*. As a method for introducing a recombinant vector into a yeast host, electroporation method, spheroblast method, and lithium acetate method can be exemplified.

Types of a host plant (cell, tissue, individual) to be used for preparing a transgenic plant (cell, tissue, individual) are not particularly limited, and can be appropriately selected from: a petal, fruit plant, vegetable, edible root, cereal, foliage plant, timbers including fruit tree, for example plants of the genus *Solanum, Poaceae, Brassicaceae, Asteraceae, Pedaliaceae, Resedaceae, Myrtaceae, Rosaceae, Leuminosae, Arecaceae*, or *Rubicaceae*; cultured cells, or tissues (seeds, callus) of these plants. For preparing these transgenic plants, a method for introducing a genetic DNA of the present invention into a genomic DNA of a plant cell, by using the above recombinant vector of the present invention comprising a gene of the present invention, and introducing the recombinant vector into a plant cell, can be applied. Transformation of a plant can be performed by applying known methods including Leafdisk cocultivation method, electroporation method, *agrobacterium* method, and particle gun method, according to the type of plants, etc. Alternatively, a method for preparing a transgenic plant by incorporating directly a recombinant vector of the present invention into a receptor cell by enhancing physically or chemically the permeability of a plant cell.

A molybdenum-fortified food or food material of the present invention is not particularly limited as long as it is a food or food material supplemented with a transformant of the present invention such as transgenic yeast or transgenic plant (cell, tissue, individual) combining molybdenum, or a treated material thereof. A transformant expressing a molybdenum transporter such as yeast, combined with molybdenum can be added to a food or food material, and used as a food or food material having a function of preventing/treating Mo deficiency. Types of food or food material of a molybdenum-fortified food or food material used for preventing/treating Mo deficiency are not particularly limited, and examples include: various beverages including yoghurt, drinkable yoghurt, juice, milk, soy milk, alcohols, coffee, black tea, boiled tea, oolong tea, or sport drink; baked cakes including cream caramel, biscuits, bread, cake, jelly, and senbei (japanese rice cracker); Japanese cake including sweet bean jelly; breads/snacks including cold dessert and chewing gum; noodles including wheat noodle and buckwheat noodle; fish cakes including steamed fish paste, ham, fish meat sausage; seasonings including soybean paste (miso), soybean sauce, dressing, mayonnaise, sweetener; dairy products including cheese and butter; various prepared foods including tofu, konjac, fish boiled in soy sauce, jiao-zi, croquette and salad. Not only a transformant expressing the above-mentioned molybdenum transporter such as yeast, and combined with molybdenum, but also treated materials thereof including ground materials, dried materials, dried ground materials, extracted materials and enzymatically treated materials can be added to these foods, or food materials.

A molybdenum-fortified feed of the present invention is not particularly limited as long as it is a feed to which a transgenic yeast or transgenic plant (cell, tissue, individual) or a treated material thereof is added. A transformant expressing a molybdenum transporter such as yeast, and combined with molybdenum, can be used as material for feed, that can be used advantageously for breeding domestic animals/fowls such as pig, cattle, chicken; pets such as dog or cat; cultured fish and shellfish, when compounded to basic feed. As the above basic feed materials, rice bran, wheat bran, bean cake, soy germ, soy sauce cake, potato pulp, konjac paste, palm oil residue, calcium-containing material, starch, can be used. As a calcium-containing material, a mixture of one or more selected from: egg shell, oyster shell, calcium carbonate, calcium lactate, calcium phosphate, calcium propionate, etc. can be exemplified. Examples of starch include corn, sorghum, other cereals for feed, ocarina starch, potato starch, cornstarch, wheat starch, tapioca or sago starch, various treated starch, glucose, isomerized sugar, and starch syrup. Not only a transformant expressing the above-mentioned molybdenum transporter such as yeast, and combined with molybdenum, but also treated materials thereof including ground materials, dried materials, dried ground materials, extracted materials and enzymatically treated materials can be added to these feeds.

A method for screening a material promoting or suppressing molybdenum transporter activity of the present invention is not particularly limited as long as it is a method for measuring/estimating the incorporation level of molybdenum into a cell, comprising allowing the transformant in which a recombinant vector is introduced, and expressing a molybdenum transporter to contact $MoO_4^{2-}$ in the presence of a test substance. The above transformant can be exemplified by yeast, plant cell, and plant. Mo concentration in yeast cell can be performed according to a method described previously (Takano, J., Noguchi, K., YasuMori, M., Kobayashi, M., Gajdos, Z., Miwa, K., Hayashi, H., Yoneyama, T. and fujiwara, T. (2002) *Arabidopsis* boron transporter for xylem loading. Nature 420: 337-340). At the time of measurement/estimation, it is preferable to compare with a cell of a same type, in which no molybdenum transporter is expressed.

In the following, the present invention will be described in detail by referring to the Examples, while the technical scope of the present invention will not be limited to these exemplifications.

EXAMPLE 1

Materials and Methods

[Growth of Plants]

In the present experiment, *Arabidopsis thaliana* accessions Col-0 and Ler and a recombinant inbred (RI) line obtained by crossing the same (Lister and Dean, 1993) were used. Stocks in the laboratory were used for Col-0 and Ler. RI lines were distributed from Nottingham *Arabidopsis* Stock Centre. Moreover, SALK_069683 and SALK_118311, foreign gene fragment (T-DNA)-introduced knockout strains, were distributed from SALK institute as mutants. Background of these mutants is Col-0.

Cultivation of *Arabidopsis thaliana* was performed by modifying a part of a method described previously (Hirai, M. Y., Fujiwara, T., Chino, M. and Naito, S. (1995) Effects of sulfate concentrations on the expression of a soybean seed storage protein gene and its reversibility in transgenic *Arabidopsis thaliana*. Plant Cell Physiol. 36: 1/331-1/339). Seeds were inoculated on Rockwool (Nittobo Co., Tokyo, Japan) arranged on a plastic tray, and were treated by vernalization for 48 hours or more at 4° C. Cultivation was performed with an artificial weather control equipment, by lighting with a fluorescent lamp under a cycle of 10 hours light period/14 hours dark period, at 22° C. MGRL (Fujiwara, T., Hirai, M.Y., Chino, M., Komeda, Y. and Naito, S. (1992) Effects of sulfur nutrition on expression of the soybean seed storage protein genes in transgenic petunia. Plant Physiol. 99: 263-268) water culture solution was used as a water culture solution. Plastic trays were rinsed with deionized water every 3 days, to change the water culture solution. The MGRL water culture solution contains $1.7 \times 10^2$ nM $MoO_4^{2-}$.

[Measurement of Mo Concentration in *Arabidopsis thaliana* Leaves]

Preparation of a Sample for Measuring Mo Concentration in *Arabidopsis thaliana* leaves was performed as described previously (Noguchi, K., YasuMori, M., Imai, T., Naito, S., Matsunaga, T., Oda, H., Hayashi, H., Chino, M. and Fujiwara, T. (1997) bor1-1, an *Arabidopsis thaliana* mutant that requires a high level of boron. Plant Physiol. 115: 901-906). 3 leaves among the 5th to 9th leaves of an individual wherein 11-1/3 true leaves have developed, were used for measurement. Samples were dried for 48 hours or more at 80° C., and the dried weight was measured. Samples were transferred in a Teflon (registered trademark) tube, and decomposed at 1/30° C. by using 2 ml of nitric acid per sample. Samples after nitric acid decomposition were dissolved in 1.5 ml of 0.08 N nitric acid containing 5 ppb of indium as an internal standard material. Mo concentration was measured by using an inductively coupled plasma mass spectrometry (ICP-MS; SEIKO, Chiba, Japan) according to a method described in the manual attached to ICP-MS.

[Genetic Analysis]

DNA extraction from *Arabidopsis thaliana* to be used for genetic analysis was performed as described previously (Kasajima, I., Ide, Y., Ohkama-Ohtsu, N., Hayashi, H., Yoneyama, T. and Fujiwara, T. (2004) A protocol for rapid DNA extraction from *Arabidopsis thaliana* for PCR analysis. Plant Mol. Biol. Rep. 22: 49-52). According to genetic polymorphism data between Col-0 and Ler, which was reported previously (Jander, G., Norris, S. R., Rounsley, S. D., Bush, D. F., Levin, I. M. and Last, R. L. (2002) *Arabidopsis* map-based cloning in the post-genome era. Plant Physiol. 129: 440-450), primers that amplify regions containing SSLP by PCR (polymerase chain reaction) were constructed. Primers used for PCR are shown in Table 1.

TABLE 1

| Type of experiment | targeted gene or sequence | | Primer sequence |
|---|---|---|---|
| Mapping | T28124 | upstream | 5'-GACAGAGAGCCCATTTGGTG-3' |
| | | downstream | 5'-TCGCTTAGTATCGCTTCGAG-3' |
| | F27A10 | upstream | 5'-TCATACAGCTTTAATACCAATCAGTAA-3' |
| | | downstream | 5'-CAGTTTGTGTACGGGATGAA-3' |
| | F13B15_01 | upstream | 5'-CAATTTCCGACGGTTGAATA-3' |
| | | downstream | 5'-CCATCCCGCGACTTCTATATG-3' |
| | F13B15_02 | upstream | 5'-CCAAACTTTTATTTTCTCCACTAACAA-3' |
| | | downstream | 5'-CGATGTTTGTCACTGCTCTG-3' |
| | F3N11_01 | upstream | 5'-ATTCCGGTGAACCTAGAACG-3' |
| | | downstream | 5'-TCAGATACTGTCGCCATCAAG-3' |
| | F3N11_02 | upstream | 5'-AATGCACGCACCCTTCTACT-3' |
| | | downstream | 5'-GGTTGATAACTTGCGGCTTT-3' |
| | F17B15 | upstream | 5'-AGGCAATGTGCTTATGTCAAA-3' |
| | | downstream | 5'-CCTCATATTTGGATTGGGTTG-3' |
| | T19L18 | upstream | 5'-TTTCGAGTTTGGACATTGGA-3' |
| | | downstream | 5'-GCTTTGGTGCAAATTAATACCC-3' |
| T-DNA determination of insertion site | SALK T-DNA (pROK2) | LBb1 | 5'-GATGGCCCACTACGTGAACCCAT-3' |
| | | RB | 5'-TAGTGACCTTAGGCGACTTTT-3' |
| | SALK_118311 | LP1 | 5'-TCGGGGAACAGATCATACGACA-3' |
| | | RP1 | 5'-CCGAAACGTTCTAGGTTCACCG-3' |
| | SALK_069683 | LP2 | 5'-CGCGTTGTATATGCCGGTGAA-3' |
| | | RP2 | 5'-CGAATGTTCAAGACTACCGGAAACA-3' |
| Subcloning | At2g25680 | genomic ORF 5' (Sal I-Eco RI) | 5'-ACGCGTCGACGAATTCACAATGGAGTCTCAGTCTCAGAGA-3' |
| | | genomic ORF 3' (Xho I) | 5'-CCGCTCGAGTCAAGCATGTTCACCGGATT-3' |
| | | genomic ORF 3' (Bam HI) | 5'-CGGGATCCGCCTCCTCCAGCATGTTCACCGGATTG-3' |
| | | promoter 5' (Bam HI) | 5'-CGGGATCCTTTCGAAATGAGATCCGA-3' |
| | | promoter 3' (Nco I) | 5'-GACTCCATGGTTTCTGTTTTGT-3' |

Strains to be used for genetic analysis were always cultivated together with plural number of Col-0 and Ler. When measuring Mo concentration, Mo concentration of Col-0 and Ler as well as that of the sample were measured. By using the intermediate value of MO concentration of Col-0 and Ler cultivated simultaneously as a standard, strains were discriminated as those having a higher Mo concentration than the standard (High), and those having a lower Mo concentration than the standard (Low).

[Preparation of a Construct]

Constructs used in the present examples were prepared according to the following procedure. The list of constructs prepared is shown in FIG. 1. See Table 1 for primers used for preparing constructs. The plasmid names and preparation methods thereof are described in the following.

(1) pHT010 (CaMV35SO::At2g25680 (genomicORF)::SGFP (Synthetic GFP))

1) ORF of At2g25680 was amplified with a combination of primers of genomic ORF 5' (SalI-EcoRI) and genomic ORF 3' (BamHI) (see Table 1), by using a genomic DNA of Col-0 as a template.
2) The amplified product was introduced in top GEM-T Easy Vector (Promega) by TA cloning method (designated as pHT002).
3) It was confirmed by a nucleotide sequence analysis that the introduced sequence is conform to an ORF of At2g25680.
4) pHT002 was cleaved with SalI and BamHI, and introduced into pTF486 which was cleaved with SalI and BamHI (designated as pHT010).

(2) pHT007 (Triose Phosphate Isomerase Promoter::At2g25680 (Genomic ORF))

1) ORF of At2g25680 was amplified with a combination of primers of genomic ORF 5' (SalI-EcoRI) and genomic ORF 3' (XhoI) (see Table 1), by using a genomic DNA of Col-0 as a template.
2) The amplified product was introduced into pGEM-T Easy Vector (Promega) by TA cloning method (designated as pHT001).
3) It was confirmed by a nucleotide sequence analysis that the introduced sequence is conform to an ORF of At2g25680.
4) pHT001 was cleaved with EcoRI and XhoI, and introduced into pYX222x (distributed from Dr. Beom-Seok Seo of Iowa Sate University) which was cleaved with EcoRI and XhoI (designated as pHT0007).

(3) pHT005 (At2g25680 Promoter (2903 bp)::GUS)

1) By using a genomic DNA of Col-0 as a template, a 2903-bp region was amplified toward upstream from the initiation codon of At2g25680 with a combination of primers of promoter 5' (BamHI) and promoter 3' (NcoI) (see Table 1).
2) The amplified product was cleaved with BamHI and NcoI, and introduced into pTF537 (prepared by Dr. Fujiwara of Laboratory of Plant Function Engineering) which was cleaved with BamHI and NcoI (designated as pHT003).
3) pHT 003 was cleaved with BamHI and NotI, and introduced into pTkan+ which was cleaved with BamHI and ApaI (designated as pHT005).

(4) pHT006 (At2g25680 Promoter (2903 bp)::sGFP)

1) By using a genomic DNA of Col-0 as a template, a 2903-bp region was amplified toward upstream from the initiation codon of At2g25680 with a combination of primers of promoter 5' (BamHI) and promoter 3' (NcoI) (see Table 1).
2) The amplified product was cleaved with Bam HI and NcoI, and introduced into pTF538 which was cleaved with BamHI and NcoI (designated as pHT004).

3) pHT 003 was cleaved with BamHI and NcoI, and introduced into pTkan+ which was cleaved with BamHI and ApaI (designated as pHT006).

[Analysis of Intracellular Localization of AT2G25680]

In order to investigate the intracellular localization of translated products of At2g25680, intracellular localization of a fusion protein of AT2G25680 and GFP was observed. First, a construct (pHT010; see FIG. 1) for expressing a fusion protein of a translated product of AT2G25680 and GFP was prepared under control of cauliflower mosaic virus 35SRNA promoter in a plant cell. Next, gold particles attached with this plasmid were introduced into onion epidermal cells with a helium-gas-driven particle accelerator (PDS-1000/He; Bio-Rad) at a helium pressure of 7.6 Mpa, by making the vacuum in the chamber as 28 inches Hg. Onion epidermal cells after introduction were placed on a filter paper impregnated with MGRL water culture solution, and was allowed to rest for 12 hours at a dark place of 22° C. GFP fluorescence of the onion epidermal was observed according to a method described previously (Takano, J., Noguchi, K., YasuMori, M., Kobayashi, M., Gajdos, Z., Miwa, K., Hayashi, H., Yoneyama, T. and Fujiwara, T. (2002) *Arabidopsis* boron transporter for xylem loading. Nature 420: 337-340).

[Yeast Growth]

Yeast (*Saccharomyces cerevisiae*) used in the present experiment is BY4741 strain (MATa his2DO met 15DO ura3DO). Culture of yeast was preformed according to common procedures. $Na_2Mo_4$ was removed from a minimal medium of Sherman (2002), and 2% glucose, 20 mg/l Ade, 30 mg/l L-Leu, 20 mg/l Met, 20 mg/l Ura and 20 mg/l L-Trp was supplemented, and the resultant was used as a medium (hereinafter sometimes referred to as "—MoSD medium").

[Yeast Transformation]

Yeast transformation was performed by a modified procedure of lithium acetate method (Rose, M. D., Winston, F. and Heiter, P. (1990) Methods in Yeast Genetics. Cold Spring Harbor, N.Y.: Cold Spring Harbor Laboratory Press). The procedures were as follows.

(1) 1.5 ml of yeast culture solution with an $OD_{600}$ level of approximately 0.4 was centrifuged at 1/3000 rpm at 4° C. for 5 sec to remove the supernatant.
(2) The resultant was washed twice with sterile water. 750 µl of sterile water was used for the first wash, and 100 µl for the second.
(3) 50 µl of TE/LiAc buffer [5 ml of 10×TE (pH 7.5), 5 ml of 1M LiAc (pH 7.5), 40 ml of sterile water] was added and well suspended. The resultant was centrifuged at 1/3000 rpm at 4° C. for 5 sec to remove the supernatant.
(4) 50 µl of TE/LiAc buffer was added and well suspended, and 210 µl of PEG/LiAc buffer [5 ml of 10×TE (pH 7.5), 5 ml of 1M LiAc (pH7.5), 40 ml of 50% (w/v) PEG400] was added. 5 µl of Salmon Sperm DNA [1 ml of TE (pH 7.5) was added to 6 mg of DNA, and stirred for one day and night at 37° C.] and 5 µl of plasmid (1 µg) were further added, and well suspended.
(5) The resultant was allowed to rest for 30 min in a room of a constant temperature of 30° C.
(6) The resultant was allowed to rest for 15 min on a heat block of 42° C., and then centrifuged at 1/3000 rpm at 4° C. for 10 sec, to remove the supernatant.
(7) 100 µl of sterile water was added and strains were inoculated on a solid medium.

[Measurement of Transport Activity Using Yeast]

A construct (pHT007; see FIG. 1) for overexpressing At2g25680 under control of a triose phosphate isomerase promoter in yeast, was prepared. Next, the construct was introduced into yeast (*Saccharomyces cerevisiae*, BY4741) by transformation using a modified procedure of lithium acetate method, to obtain a transgenic strain. Similarly, a At2g25680 free-vector alone was introduced into yeast to obtain a control strain. A single colony of a transgenic strain and of a control strain were inoculated onto a —MoSD liquid medium separately, and cultured by shaking at 30° C. at 300 rpm.

Measurement of Mo concentration in yeast strains was performed by partly modifying a method described previously (Takano, J., Noguchi, K., YasuMori, M., Kobayashi, M., Gajdos, Z., Miwa, K., Hayashi, H., Yoneyama, T. and Fujiwara, T. (2002) *Arabidopsis* boron transporter for xylem loading. Nature 420: 337-340). By using the optical density at 600 nm as an index, the cell density of a transgenic strain and control strain was arranged so that the $OD_{600}$ level becomes 0.5, and cells in 30 ml of the culture solution were recovered by centrifugation. The recovered cells were re-suspended into 20 ml of —MoSD liquid medium, or —MoSD liquid medium containing $1.7 \times 10^2$ nM of $MoO_4^{2-}$, and cultured by shaking at 30° C. at 300 rpm for 30 min. Cells were recovered by further centrifugation, washed twice by using an ice-cooled milliQ, and dried directly. The cells were dried at 80° C. for 48 hours or more, and the dried weight was measured. Measurement of Mo concentration in yeast cells was performed in the same manner as the measurement of Mo concentration in *Arabidopsis thaliana* leaves.

[Analysis of Expression Tissues of At2g25680]

In order to investigate tissues in which At2g25680 is expressed, a construct (pHT006; see FIG. 1) to which β-glucuronidase (GUS) gene is linked in a 2903-bp promoter region toward upstream from the initiation codon of At2g25680, was prepared. *Agrobacterium* (*Agrobacterium tumefaciens*, GV3101; Koncz, C. and Schell, J. (1986) The promoter of TL-DNA gene 5 controls the tissue specific expression of chimeric genes carried by a novel type of *Agrobacterium* binary vector. Mol. Gen. Genet. 204: 383-396) was used to transform it into a wild type of *Arabidopsis thaliana* (Col-0) by a vacuum infiltration method (Clough, S. J. and Bent, A. F. (1998) floral dip: a simplified method for *Agrobacterium*-mediated transformation of *Arabidopsis thaliana*. Plant J. 16: 735-743). Seeds obtained from the transgenic strain were inoculated on a solid medium containing 250 mg/l of ClaForan, 50 mg/l of Kanamycin, 8 g/l of Agar and mixed salts for Murashige & Skoog medium (Wako, Osaka, Japan) with half of usual concentration, to obtain seeds from strains which showed Kanamycin resistance for use as a transgenic strain. GUS staining, segment preparation, and observation of a transgenic strain were performed according to a method described previously (Shibagaki, N., Rose, A., McDermott, J. P., Fujiwara, T., Hayashi, H., Yoneyama, T. and Davies, J. P. (2002) Selenate-resistant mutants of *Arabidopsis thaliana* identify Sultr1;2, a sulfate transporter required for efficient transport of sulfate into roots. Plant J. 29: 475-486).

The construct (pHT 005; see FIG. 1) to which GFP gene is linked in a 2093-bp promoter region toward upstream from the initiation codon of At2g25680, was similarly transformed to *Arabidopsis thaliana*. Observation of GFP fluorescence was performed according to a method described previously (Takano, J., Noguchi, K., YasuMori, M., Kobayashi, M., Gajdos, Z., Miwa, K., Hayashi, H., Yoneyama, T. and Fujiwara, T. (2002) *Arabidopsis* boron transporter for xylem loading. Nature 420: 337-340).

[Determination of the Michaelis Constant of a Molybdenum Transporter]

Michaelis constant (Km) is a substrate concentration of when the substrate transport velocity of a transporter is half of the maximum value, and is a specific value for each transporter. Specifically, in the present invention, Km is the Molybdenum concentration of a medium, when the velocity of a molybdenum transporter transporting molybdenum from a medium into a cell becomes half of the maximum velocity. This value describes an important characteristic of the transporter, suggesting in which aspect the transporter exhibits its effect for application or actual use.

Measurement of Mo concentration in yeast cells were performed by modifying a part of a method described previously (Takano, J., Noguchi, K., YasuMori, M., Kobayashi, M., Gajdos, Z., Miwa, K., Hayashi, H., Yoneyama, T. and Fujiwara, T. (2002) *Arabidopsis* boron transporter for xylem loading. Nature 420: 337-340). By using the optical density at 600 nm as an index, the approximate cell density of a transgenic strain (pHT007) and control strain was arranged so that the $OD_{600}$ level becomes 0.5, and cells in 40 ml of the culture solution were recovered by centrifugation. The recovered cells were re-suspended into 20 ml of —MoSD liquid medium, or —MoSD liquid medium containing $6.4 \times 10$, $7.5 \times 10$, $9.0 \times 10$, $1.1 \times 10^2$, $1.5 \times 10^2$, $2.2 \times 10^2$, $7.4 \times 10^2$ or $1.6 \times 10^3$ nM of $MoO_4^{2-}$, and cultured by shaking at 30° C. at 30 rpm for 30 min. Cells were recovered by further centrifugation, washed twice by using an ice-cooled milliQ, and dried directly. The cells were dried at 80° C. for 48 hours or more, and the dried weight was measured. Measurement of Mo concentration in yeast cells was performed in the same manner as the measurement of Mo concentration in *Arabidopsis thaliana* leaves.

The results are shown by plotting actual measurement values on a graph, in which the vertical axis indicates a reciprocal of molybdenum transport velocity (1/[Molybdenum transport velocity]), and the horizontal axis indicates a reciprocal of Molybdenum concentration in the medium (1/[Molybdenum concentration in the medium]). Michaelis constant of a molybdenum transporter was determined, according to the fact that the intersection point value of the horizontal axis with a straight line connecting by plotting experimental results on the graph is −1/Km, from a formula called Michaelis-Menten in chemical kinetics.

[Growth of *Arabidopsis thaliana* in a Molybdenum-deficient Environment]

Molybdenum is used in plants, for example as a constituent of enzyme necessary for growth, and a certain level of Molybdenum is indispensable for a plant to live. Plants incorporate Molybdenum from soil into its body, and have a system to transport Molybdenum to organs/tissues in need thereof. If a Molybdenum transporter plays a role for transport, in a plant in which the Molybdenum transporter does not function normally, the Molybdenum transport system will have a trouble, leading to an abnormality in growth.

A wild type of *Arabidopsis thaliana* (Col-0) and the aforementioned *Arabidopsis thaliana* mutant (SALK_118311) which can not generate a normal Molybdenum transporter due to an introduction of T-DNA, a foreign gene, to a gene of Molybdenum transporter, were cultured in the presence and absence of Molybdenum, to compare their growth.

Cultivation of *Arabidopsis thaliana* was performed by modifying a part of a method described previously (Hirai, M. Y., Fujiwara, T., Chino, M. and Naito, S. (1995) Effects of sulfate concentrations on the expression of a soybean seed storage protein gene and its reversibility in transgenic *Arabidopsis thaliana*. Plant Cell Physiol. 36: 1/331-1/339). Seeds were inoculated on a solid medium in which Sucrose 1%, Gellan Gum 1.2% were supplemented to a MGRL (Fujiwara, T., Hirai, M. Y., Chino, M., Komeda, Y. and Naito, S. (1992) Effects of sulfur nutrition on expression of the soybean seed storage protein genes in transgenic petunia. Plant Physiol. 99: 263-268) water culture solution, or a water solution in which $(NH_4)_6Mo_7O_{24} \cdot 4H_2O$ was removed from a MGRL water culture solution, and were treated by vernalization for 48 hours or more at 4° C. These solid media contain $1.7 \times 10^2$ nM, or between 2.0-9.0 nM of $MoO_4^{2-}$. Cultivation was performed with an artificial weather control equipment, by lighting with a fluorescent lamp lighting under a cycle of 10 hours light period/14 hours dark period, at 22° C.

[Measurement of Transport Activity Using Yeast Related to MoTR1 Homologous Gene of *Oryza sativa*]

(1) OsMoTR1 Expression Vector
1) By using a genomic DNA of *Oryza sativa* (*Oryza sativa* L. cv. Nipponbare) as a template, ORF of Os08g01120 was amplified with a combination of primer attB1 9636.m0012 (5'-aaaaagcaggcttaggcgagcagagaagagaaga-3': SEQ ID NO: 50) and primer attB2 9636.m00012 (5'-agaaagctgggt-gcggaacgagctgtattgagt-3':SEQ ID No: 51).
2) The amplified product was introduced into pDONR/ZeO vector (Invitrogen) by BP reaction (designated as OsMoTR2 entry vector).
3) It was confirmed by a nucleotide sequence analysis that the introduced sequence is conform to an ORF of Os08g01120.
4) OsMoTR1 entry vector was recombined with pYES-DEST52 vector (Invitrogen) by LR reaction (designated as OsMoTR1 expression vector).

(2) OsMoTR2 Expression Vector
1) By using a genomic DNA of *Oryza sativa* (*Oryza sativa* L. cv. Nipponbare) as a template, CDS of Os01g45830 was amplified with a combination of primer attB1 m04384-ATG (5'-aaaaagcaggctatatggcatcctccgccggcga-3': SEQ ID NO:52) and primer attB2 m04384 (5'-agaaagctgggtatcaag-catctccagccccat-3' SEQ ID NO:53).
2) The amplified product was introduced into pDONR/Zeo vector (Invitrogen) by BP reaction (designated as OsMoTR2 entry vector).
3) It was confirmed by a nucleotide sequence analysis that the introduced sequence is conform to a CDS of Os01g45830.
4) OsMoTR2 entry vector was recombined with pYES-DEST52 vector (Invitrogen) by LR reaction (designated as OsMoTR2 expression vector).

(3) Yeast Growth
Yeast (*Saccharomyces cerevisiae*) used in the present experiment was BY4741 strain (MATa his2DO met 15DO ura3DO). Culture of yeast was preformed according to common procedures. $Na_2Mo^4$ was removed from a minimal medium of Sherman (2002), and 2% galactose, 30 mg/l L-Leu, 20 mg/l Met, 20 mg/l H is and 20 mg/l L-Trp was supplemented, and the resultant was used as a medium (hereinafter sometimes referred to as "—MoSD medium"). However, except for [Measurement of transport activity using yeast] a medium in which 2% galactose was replaced with 2% glucose was used. Transformation was performed in the same manner as in the above.

(4) Measurement of Transport Activity Using Yeast
Constructs (OsMoTR1 expression vector and OsMoTR2 expression vector) for overexpressing Os08g01120 or Os01g45830 were prepared under control of GAL1 promoter in yeast. Next, the construct was introduced into yeast (*Saccharomyces cerevisiae*, BY4741) by transformation using a modified procedure of lithium acetate method, to obtain a transgenic strain. Similarly, pYES2 vector was introduced into yeast, to obtain a control strain. A single colony of a transgenic strain and of a control cell strain were inoculated onto a separate —MoSD liquid medium, and cultured by shaking at 30° C. at 300 rpm. Measurement of Mo concentration of yeast cells was performed in the same manner as in the above.

EXAMPLE 2

Results

[QTL Analysis for Mo Concentration in *Arabidopsis thaliana* Leaves]

The present inventors compared the elemental composition of accessions Col-0 and Ler leaves, and found out that Mo concentration in Col-0 leaves was about 3 times higher compared to that of Ler. Further, by a QTL analysis using 18 strains of RI lines crossing Col-0 and Ler, they found out that QTL which dominates Mo concentration in leaves exists in a region between 2 gene markers, mi238 and er, on the upper arm of chromosome no.2.

Therefore, in order to identify the gene that determinates Mo concentration in leaves, genotypes and Mo concentration in leaves were investigated for 16 strains of RI lines having a recombination between gene markers mi 238 and er (CL 36, 59, 84, 90, 160, 177, 179, 191, 194, 237, 253, 295, 303, 358, 370, 395; Lister, C. and Dean, C. (1993) Recombinant inbred lines for mapping RfLP and phenotypic markers in *Arabidopsis thaliana*. Plant J. 4: 745-750). The results are shown in Table 2. Each RI line is shown by CL number. By using the intermediate level of Mo concentration of Col-o and Ler, which have been cultivated at the same time as RI lines as a standard, strains were discriminated as those having a higher Mo concentration than the standard (High), and those having a lower Mo concentration than the standard (Low). Genotypes were determined by a SSLP marker (C:Col-0, L:Ler, #:not clearly determined). Strains having a recombination between SNP60 and SGCSNP300 are shown as recombinant. Genetic markers exist on a chromosome, in the order of mi238, SNP60, SGCSNP300, and er. Hereinafter, the mi238 side is shown as upstream, and the er side as downstream.

TABLE 2

| RI lines | Mo con- | genotype of marker on chromosome 2 | | | | |
|---|---|---|---|---|---|---|
| CL | centration | mi238 | SNP60 | SGCSNP300 | er | |
| 36 | High | L | C | C | C | |
| 59 | Low | L | L | L | # | |
| 84 | High | L | L | C | C | recombinant |
| 90 | High | L | C | # | C | |
| 160 | Low | C | L | L | L | |
| 177 | High | L | C | L | L | recombinant |
| 179 | Low | C | L | L | L | |
| 191 | Low | C | C | L | L | recombinant |
| 194 | Low | L | # | L | C | |
| 237 | Low | L | L | L | L | |
| 253 | Low | C | # | # | L | |
| 295 | Low | L | L | L | C | |
| 303 | High | C | # | L | L | |
| 358 | Low | C | L | L | L | |
| 370 | High | # | # | C | C | |
| 395 | Low | C | C | # | L | |

Genotype of CL84 in which Mo concentration in leaves is high (showing a phenotype of Col-0 type), was recombined from Col-0 to Ler, in a region between SNP60 and SGC-SNP300. Genotype of CL 191 in which Mo concentration of leaf is low (showing a phenotype of Ler) was recombined from Ler to Col-0 in a region between SNP60 and SGC-SNP300. These results reveal that the intended gene exists in the downstream of SNP60. Further, genotype of CL 177 in which Mo concentration in leaves is high, was recombined from Col-0 to Ler in a region between mi238 and SNP60, and a region between SNP60 and SGCSNP300. This result reveals that the intended gene exists in the downstream of mi238, and in the upstream of SGCSNP300. Therefore, it was suggested that the intended gene exists in a region between SNP60 and SGCSNP300.

Further, in order to limit the region in which the intended gene exists, 21 strains having a recombination in a region between F1/3B15_01 and T19L18 were selected from 62 strains of $F_2$ generation, obtained by self-pollination of $F_1$ generation in which Col-0 and Ler were crossed. Genotypes and Mo concentration in leaves of these strains were investigated. The results are shown in Table 3. $F_2$ strains are separated according to Mo concentration, and the numbers are shown (A02-E72). As recombinants were selected, the numbers are not consequent. By using the intermediate level of Mo concentration of Col-0 and Ler, which have been cultivated at the same time as the selected strains as a standard, strains were discriminated as those having a higher Mo concentration than the standard (High), and those having a lower Mo concentration than the standard (Low). Genotypes were determined by a SSLP marker (see Table 1) (C:Col-0, L:Ler, H: hetero, #:not clearly determined, -:not tested. Strains having a recombination of Col-0 to Ler, or hetero to Ler between F1/3B15_02 and F17H15 are shown as recombinant. Genetic markers exist in the order of SNP60, F1/3B15_01, F1/3B15_02, F3N11_01, F3N11_02, F17H15, T19L18, SGCSNP300 from the upstream.

hetero in a region between F1/3B15_02 and F1/3N11, and from Ler to Col-0 in a region between F3N11_02 and F17H15. These results reveal that the intended gene exists in the downstream of F1/3B15_02, and upstream of F17H15.

From this genetic analysis, the region in which the intended gene exists has been limited to 172 kb between 2 SSLP markers, F1/3B15_02 and F17H15.

[T-DNA Insertion Site of Knockout Strain in which Foreign Gene Fragment (T-DNA) is Inserted to At2g25680]

Sulfate ion transporter homologous gene At2g25680 was present in the 172 kb-region between F1/3B15_02 and F17H15_01. This gene has a domain common with sulfate transporter, while its function was not analyzed (nonpatent document 17). As sulfur and Mo are absorbed into plants as $SO_4^{2-}$ and $MoO_4^{2-}$ (nonpatent document 9), and application of $Na_2So_4$ suppresses Mo accumulation in plants (nonpatent document 11), there was a possibility that At2g25680 homologous to sulfate ion transporter is associated with Mo absorption. Further, by comparing the At2g25680 sequence of Col-0 registered in the database (nonpatent document 14) with the sequence of Ler (Jander, G., Norris, S. R., Rounsley, S. D., Bush, D. F., Levin, I. M. and Last, R. L. (2002) *Arabidopsis* map-based cloning in the post-genome era. Plant Physiol. 129: 440-450)), it was revealed that asparagine acid, the 439 th amino acid, was replaced by balin in Ler, and 27th to 79th bases upstream of the initiation codon was deficient in Ler.

Then, 2 lines of knockout strains, SALK_118311 and SALK_069683 in which foreign gene fragment (T-DNA) was inserted to At2g25680 or its vicinity were distributed from Salk Institute. For these strains, PCR was conducted by using primers homologous to each of the nucleotide sequences upstream and downstream of the estimated T-DNA insertion site, and a primer homologous to the inner sequence of T-DNA, to select strains having an inserted gene as homo. Further, these selected strains were subjected to a nucleotide

TABLE 3

| Col-0 × Ler F2 | Mo concentration | genotype of marker on chromosome 2 | | | | | | |
|---|---|---|---|---|---|---|---|---|
| | | F13B15_01 | F13B15_02 | F3N11_01 | F3N11_02 | F17H15 | T19L18 | |
| A02 | High | — | — | C | C | C | L | |
| A08 | High | — | L | # | # | C | — | |
| B02 | High | C | C | C | C | C | L | |
| B08 | High | H | C | C | C | C | C | |
| B09 | High | H | H | H | H | C | C | |
| B15 | High | C | C | C | C | C | H | |
| B16 | High | H | C | C | C | C | — | |
| B17 | High | — | H | H | H | C | H | |
| C02 | High | H | H | H | H | H | L | |
| C05 | High | H | C | H | C | C | H | |
| C08 | High | — | L | C | C | C | — | recombinant |
| E71 | High | — | — | H | — | C | — | |
| E74 | High | — | — | H | — | C | — | |
| B04 | Low | H | L | L | L | L | H | |
| B05 | Low | C | L | L | L | L | L | |
| B12 | Low | L | L | L | L | L | C | |
| B13 | Low | H | L | L | L | L | — | |
| B14 | Low | C | L | L | L | L | C | |
| C03 | Low | C | L | L | L | L | L | |
| C10 | Low | — | H | L | L | C | — | recombinant |
| E72 | Low | — | — | L | # | C | — | |

Figure 2:
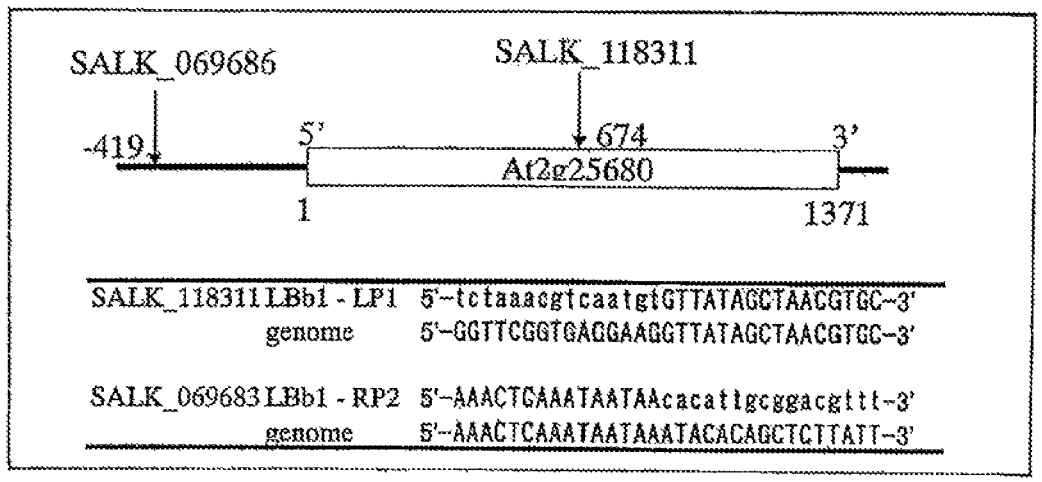
[FIG. 2]
It is a figure showing the results determining the T-DNA insertion site. PCR was performed for the knockout strains SALK_118311 and SALK_069683, in which foreign gene fragment (T-DNA) has been inserted to At2g25680 or in its vicinity, by using primers homologous to each of the nucleotide sequence upstream and downstream of the estimated T-DNA insertion site, and a primer homologous to the inner sequence of T-DNA (see Table 1), to select strains having inserted genes as homo. Further, these selected strains were subjected to a nucleotide sequence analysis near the boundary of the inserted T-DNA and genomic DNA. The 5'-3' is indicated in the ORF direction of At2g25680. The sequence shown as LBb1-LP1 or LBb1-RP2 is a part of the results of a nucleotide sequence analysis of the products amplified with each of the primers. Moreover, the sequence shown as genome is a genomic DNA sequence of *Arabidopsis thaliana*, having a high homology with the products. In the Figure, a sequence near the boundary where a gap is generated to the sequence homology, when comparing the sequences of the amplified product and genomic DNA of *Arabidopsis thaliana*, is shown. The regions in which 5 or more bases coincide are shown in capital letters, and other regions are shown in small letters. The numbers in the figure show the base number of the site in which T-DNA is inserted, when the bases are numbered from 5' to 3', and adenine in the initiation codon of At2g25680 is set as the first base.

Genotype of C08 in which Mo concentration of leaf is high was recombined from Col-0 to Ler in a region between F1/3B15_02 and F3N11. Genotype of C10 in which Mo concentration in leaves is low was recombined from Ler to sequence analysis performed in the vicinity of the inserted T-DNA and genomic DNA. By comparing with the nucleotide sequence of a wild-type, it was revealed that left border was inserted to the 674th base from the transcription initiation point in SALK_118311, and that left border was inserted to the 419th base upstream from the transcription initiation point (FIG. 2).

[Phenotype of At2g25680 Knockout Strain]

In order to investigate the influence of the At2g25680 mutation on *Arabidopsis thaliana* 's growth, phenotypes of SALK_118311 and SALK_069683 were observed. Mutate strains and wild-type Col-0 and Ler were inoculated on Rockwool, and cultured for 30 days by using MGRL water culture solution. Mo concentration contained in the MGRL water culture solution is between 2.0-9.0 nM (hereinafter referred to as "Mo-deficient condition") or $1.7 \times 10^2$ nM (hereinafter referred to as "Mo-sufficient condition").

Under Mo-deficient condition, chlorosis appeared on mutated strains leaves, and morphological abnormality showing elongated curling shape was confirmed. However, this phenotype was also observed in wild-type Col-0 and Ler. There was no difference between mutant and wild-type for the time when growth inhibition was observed in leaves and its level.

Figure 3:
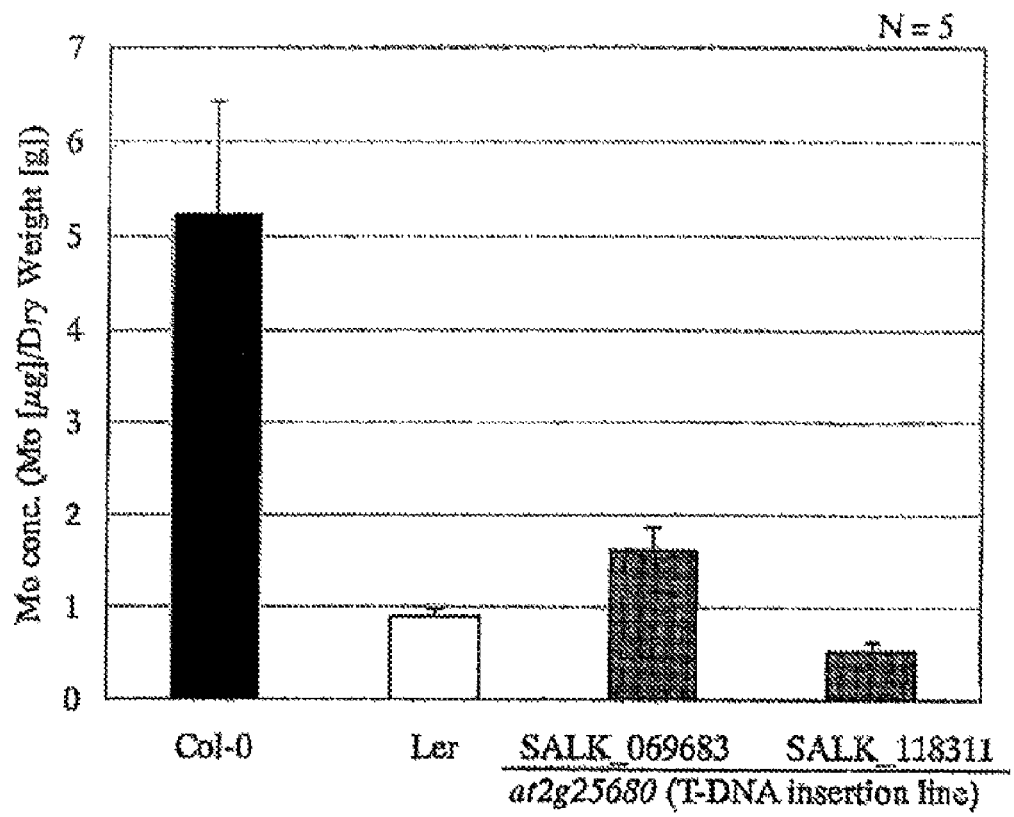
[FIG. 3]
It is a graph showing Mo concentration in leaves of At2g25680-knockout strain. SALK_118311, SALK_069683, Col-0 and Ler were inoculated on Rockwool, and cultured for 30 days by using MGRL water culture solution containing $1.7 \times 10^2$ nM $MoO_4^{2-}$. Mo concentration in leaves was measured for 5 plants in each strain, and the mean level is shown. Error bar shows the standard deviation. Mo concen-

On the other hand, no morphological abnormality was observed for mutated or wild-type strains under Mo-sufficient condition. However, by measuring Mo concentration in leaves of wild-type strains and that of mutated strains cultivated under Mo-sufficient condition, Mo concentration of mutated strains was lowered to about ⅓ of that of the wild-type strain (Col-0) Particularly, Mo concentration in SALK_118311 was lower than that of Ler (FIG. 3). Moreover, Mo concentration in leaves of $F_1$ generation obtained by crossing SALK_118311 and SALK_06983 was about ⅓ of that of Col-0, and phenotypes showing low Mo concentration were not contemplated. This result suggests that At2g25680 is a gene determining Mo concentration in *Arabidopsis thaliana* leaves.

In order to investigate the mode of inheritance of phenotype in which Mo concentration lowers in mutant leaves, phenotypes of posterity obtained by backcross breeding of At2g25680 mutated strain and a wild-type strain (Col-0) were investigated. First, each of SALK_118311 and SALK_069683 was crossed with a wild-type strain (Col-0) to obtain $F_1$ seeds. The $F_1$ generation strain was cultured for 30 days under Mo-sufficient condition, and Mo concentration in leaves was measured. Mo concentration in $F_1$ generation showed approximately an intermediate level of the concentration of mutated strain and wild-type strain, which became parent.

Figure 4:
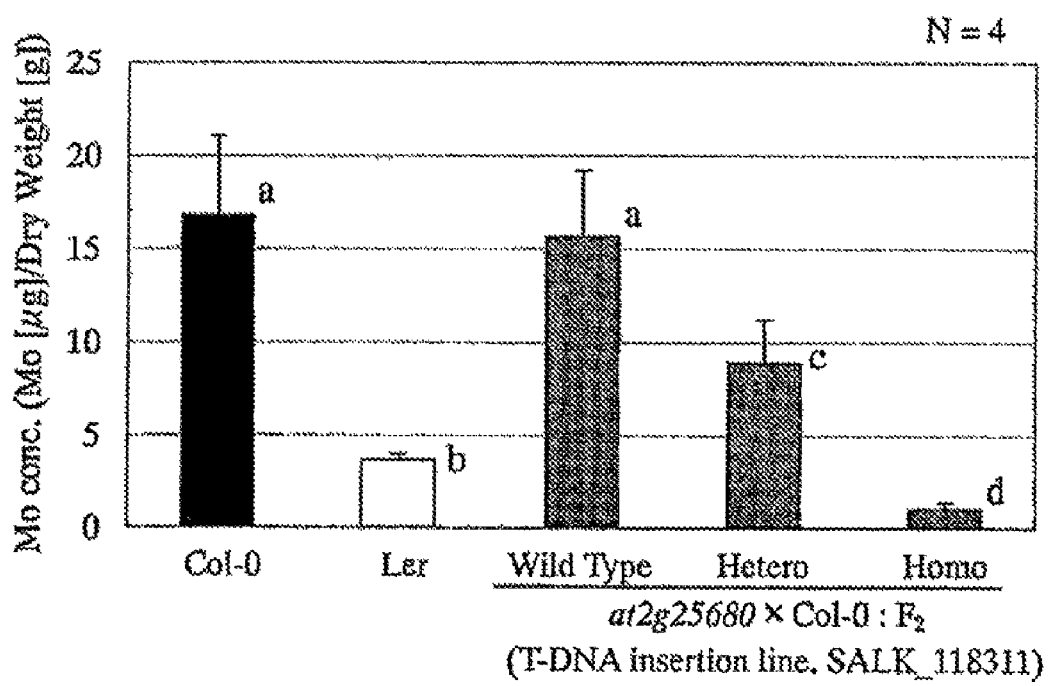
[FIG. 4]

Next, $F_2$ seeds were obtained by self-pollination of $F_1$ generation strains obtained by crossing SALK_118311 and Col-0. Mo concentration in leaves of the $F_2$ generation strains was measured in the same manner as for $F_1$ generation, and the presence/absence of T-DNA insertion into At2g25680 was confirmed by PCR. Mo concentration of strains in which T-DNA is not introduced is approximately the same as that of Col-0, and Mo concentration of strains having the inserted gene as homo, was lower than that of Ler. Moreover, Mo concentration of strains having inserted gene as hetero showed approximately an intermediate level of these strains (FIG. 4). This result support that the lowering of Mo concentration in leaves was induced by At2g25680 mutation, suggesting that the mutation is semi-dominant. From these results, it was confirmed that the cause of Mo concentration lowering in mutant strain leaves was At2g25680 mutation, and this gene was designated as MoTR1 (hereinafter, SALK_118311 is referred to as MoTR1-1, and SALK_069683 as MoTR1-2).

Meanwhile, no morphological abnormality was observed in any of the strains that were used in experiments in which cultivation was performed under Mo-sufficient condition.

[Intracellular localization of MoTR1]

Figure 5:
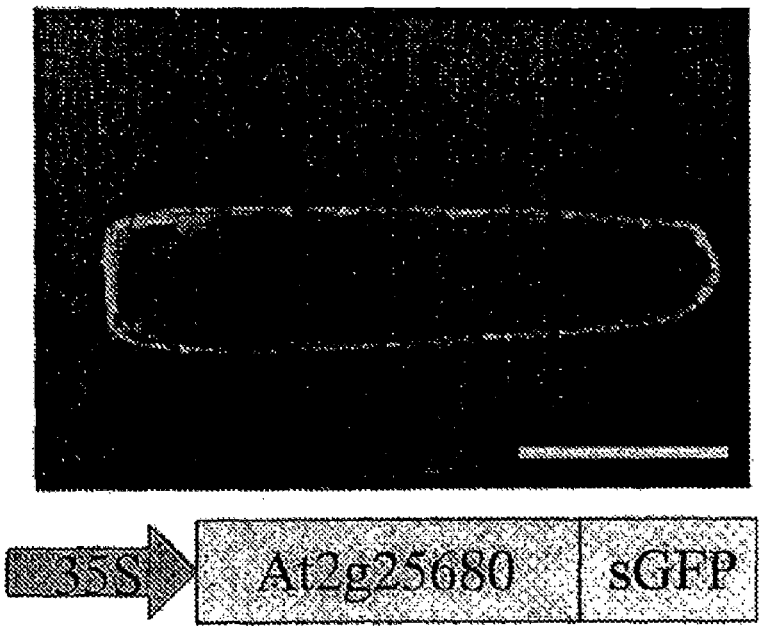

From a search in a database of membrane protein (ARAMEMNON, website address <<aramemnon.botanik.uni-koeln.de>>), it was estimated that MoTR1 has 7-12 transmembrane domains. Then, in order to investigate in which membrane of cells the translated product is localized, a construct (pHT010; see FIG. 1) for expressing a fusion protein of MoTR1 and GFP under control of cauliflower mosaic virus 35SRNA promoter was prepared and introduced into onion epidermal cell. It has been reported that GFP which is not fused with other proteins is detected in the nucleus and cytoplasm (Chiu, W., Niwa, Y., Zeng, W., Hirano, T., Kobayashi, H. and Sheen, J. (1996) Engineered GfP as a vital reporter in plants. Curr. Biol. 6: 325-330). An observation with a laser confocal microscope showed that the fluorescence of the fusion protein was localized in the external marginal part of the cell (FIG. 5). This result suggests that MoTR1 is a cell membrane protein.

[Mo Transport Activity in MoTR1]

As it was suggested that MoTR1 is a cell membrane protein, the possibility that MoTR1 has a Mo transport activity was thought. Thus, in order to investigate the Mo transport activity of MoTR1, a construct for expressing MoTR1 in yeast (pHT007; see FIG. 1) was prepared and introduced into yeast. The transgenic strain and a control strain (vector control) were inoculated on a Mo-free medium for subculture. The growth rate of the transgenic strain at that time was slower than that of the control strain. When it was subcultured so that $OD_{600}$ level becomes the same, the $OD_{600}$ level of the control strain 16 hours after subculture was approximately the same as that of the transgenic strain 19 hours after subculture.

Figure 6:
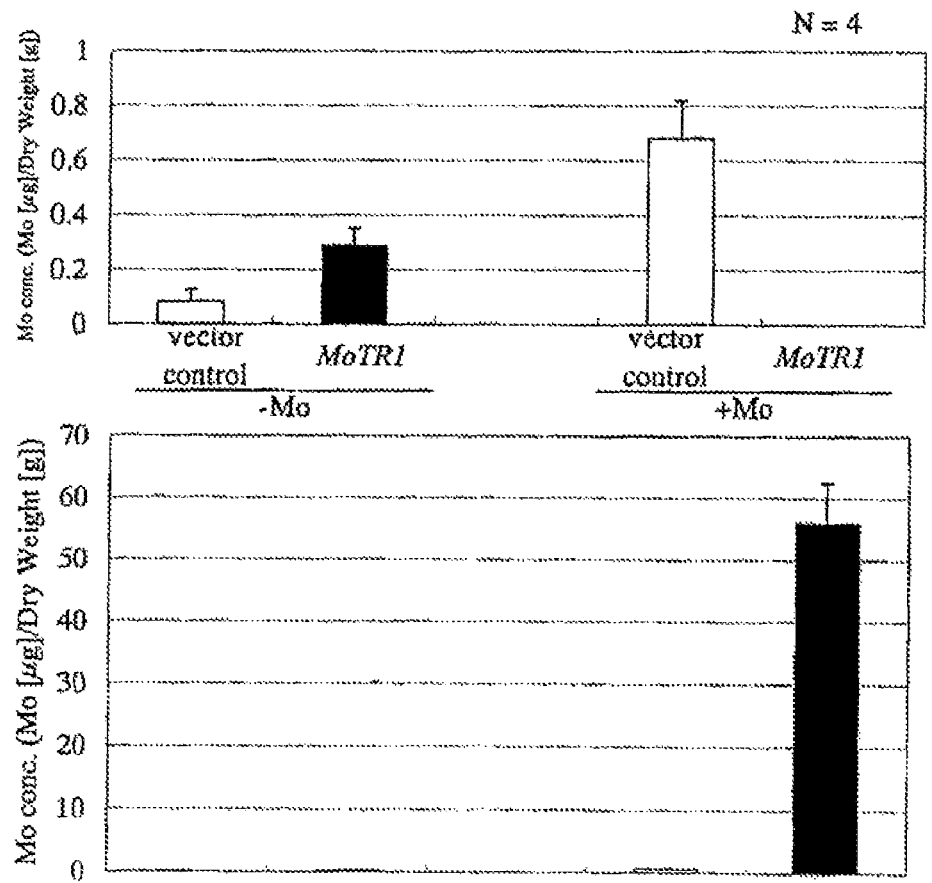

The approximate cell density of a transgenic strains and a control strain was arranged so that the $OD_{600}$ level becomes 0.5, cells recovered by centrifugation was re-suspended in a medium containing $1.7 \times 10^2$ nM of $MoO_4^{2-}$, and cultured by shaking for 30 min. By measuring the Mo concentration in cells, the concentration of the transgenic strain was increased to 80 times or more compared to that of the control strain (FIG. 6). This result suggests that MoTR1 is a Mo transporter.

[Expression Tissues of MoTR1]

In order to investigate tissues in which MoTr1 is expressed, β-glucuronidase (GUS) gene was linked to a region 2903 bp from the initiation codon of MoTr1 to transform into *Arabidopsis thaliana*. In 16 independent transgenic strains 7 days after germination, GUS activity was confirmed in leaf stalk and outer edge of leaves in aerial part (FIGS. 7B and C). In root, GUS activity was confirmed in root apex, while no activity was observed in the region 1-6 mm from root apex (FIGS. 7A and 7F). In upper part thereof, GUS activity was observed in the pericycle, and upper than the region where lateral root is observed, activity was observed in the cortex (FIGS. 7D, 7H, 7I, and 7J). When GFP was used as a reporter, the results were the same (FIGS. 7E and 7G).

[Determination of Michaelis Constant]

Figure 8:
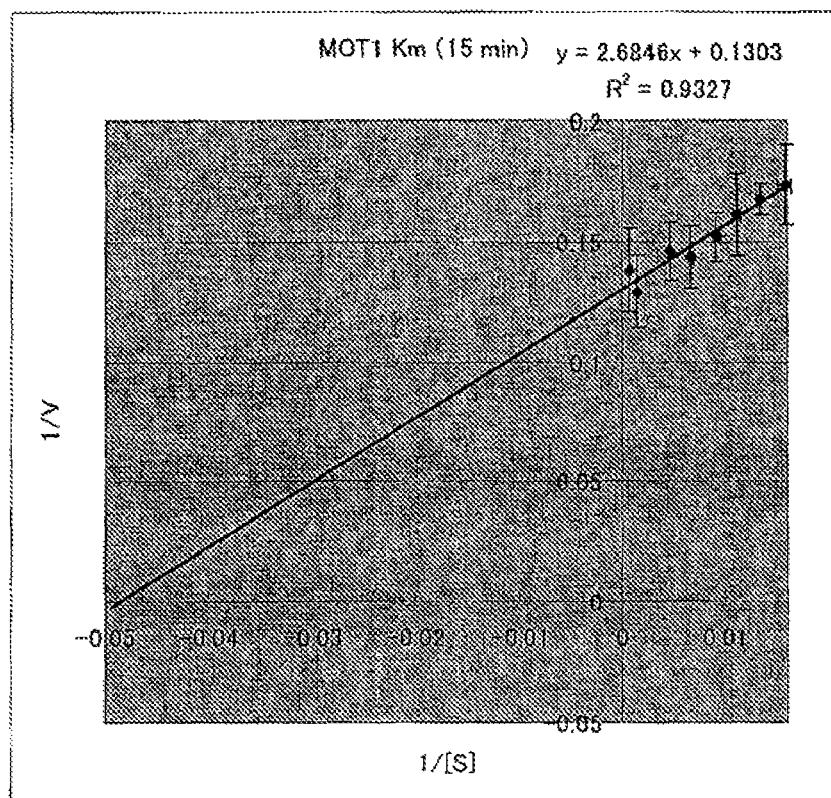

Mo concentration in yeast cultured for 15 min in a medium having an independent concentration, was 5.8, 6.0, 6.2, 6.6, 7.0, 6.9, 7.8, 7.3 (Mo [μg]/dry weight [g]), respectively, in order from the Mo medium of $6.4 \times 10$ nM. A graph was drawn, in which the vertical axis indicates a reciprocal of molybdenum transport velocity (1/[Molybdenum velocity]), and the horizontal axis indicates a reciprocal of Molybdenum concentration (1/[Molybdenum concentration in the medium]) (see FIG. 8). Straight line connecting the measurement levels by plotting was y=2.6846×0.1303 ($R^2$=0.9327), and it was revealed that Km was several dozens of nM.

[Growth of *Arabidopsis thaliana* in a Molybdenum-Deficient Environment]

Figure 9:
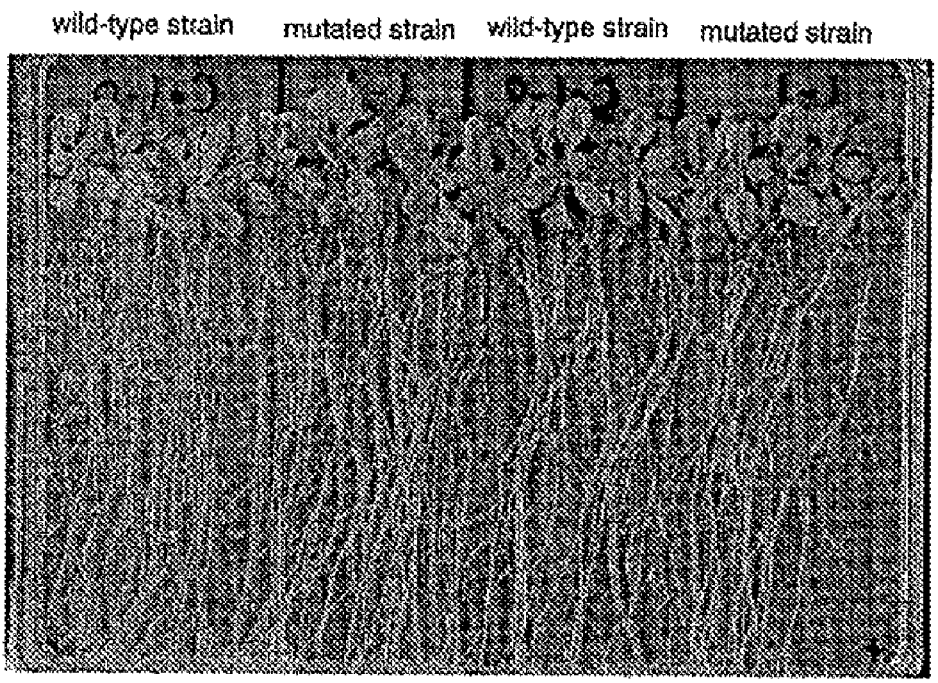
Figure 9:
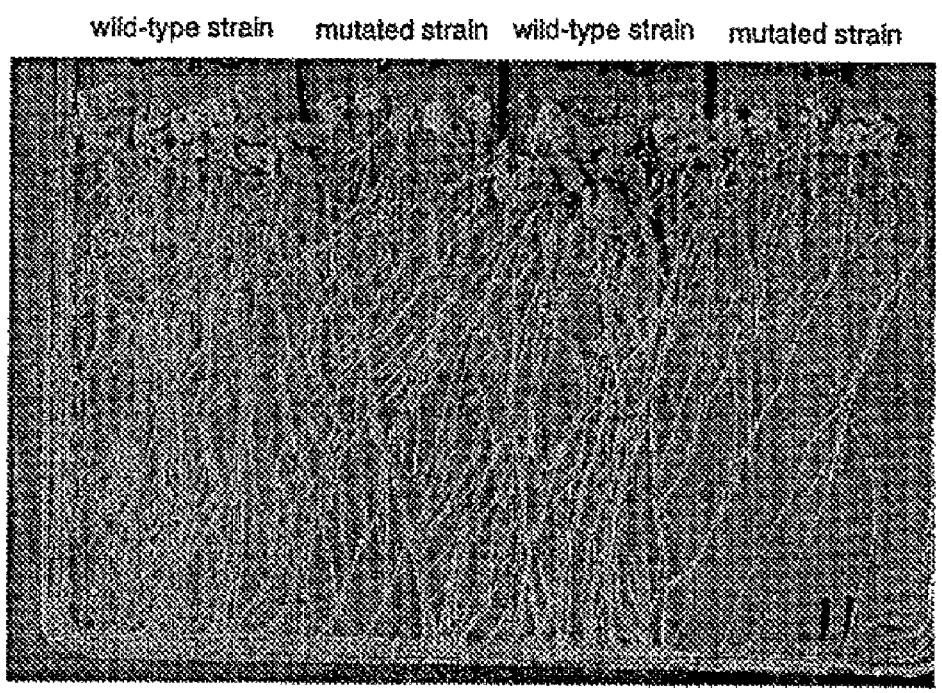

FIG. 9 shows the results of culturing *Arabidopsis thaliana* (wild-type strain, mutated strain) under each condition for 3 weeks.

In (A), the culture was performed in the presence of molybdenum, and in (B), in the absence of molybdenum. In each of the plate, 20 *Arabidopsis thaliana* were inoculated in the order of 5 wild-type strains, 5 mutated strains, 5 wild-type strains, and 5 mutated strains, from the left. In plate (A), cultured in the presence of molybdenum, wild-type strains and mutated strains showed a similar growth level, while in plate (B), cultured in the absence of molybdenum, the growth of wild-type strains was suppressed, and the growth of mutated strains was significantly suppressed.

[Transport Activity Using Yeast for *Oryza sativa* MoTR1 Homologous Gene]

Figure 10:
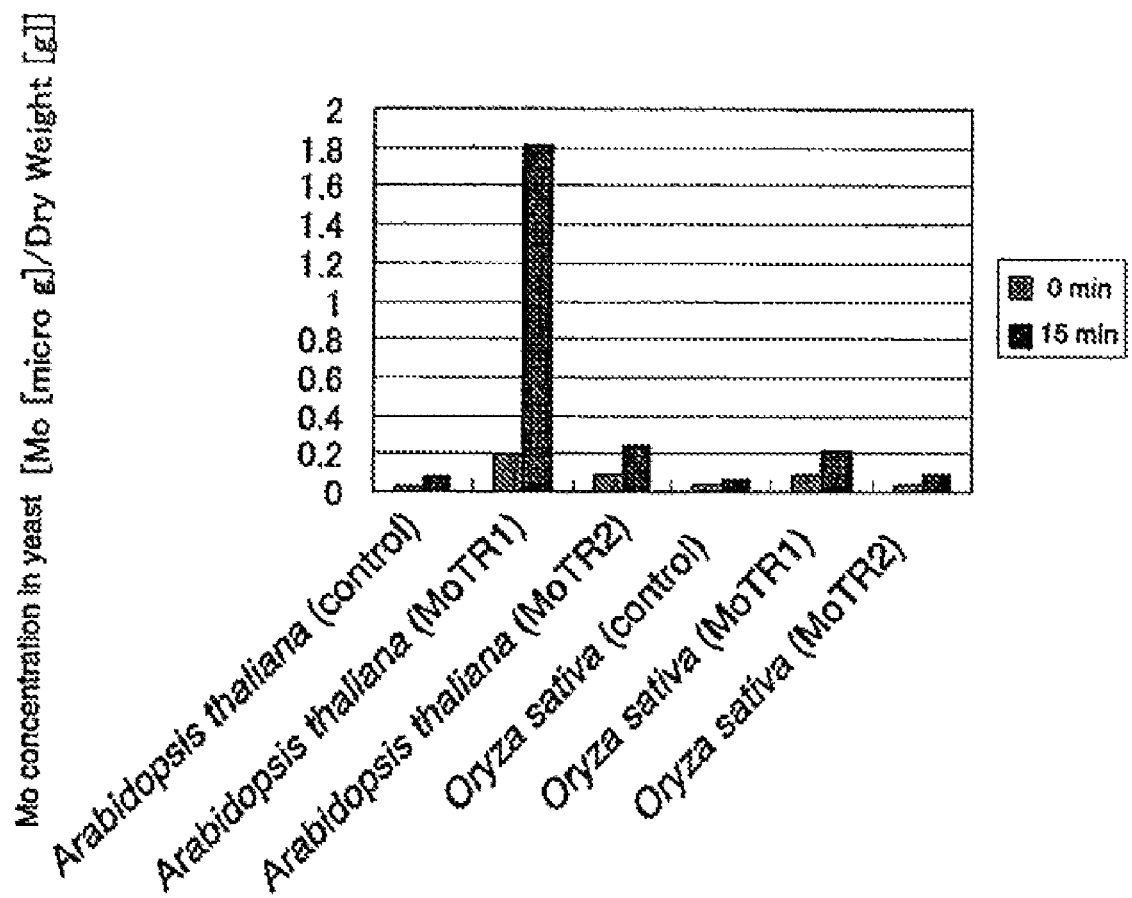

The result of study of Mo transport activity of *Oryza sativa* MoTR1, and MoTR2 is shown in FIG. 10. When incubating for 15 min in a medium containing Mo, the increase of Mo concentration in yeast expressing 2 types of *Oryza sativa* MOTR1 homologous genes was higher compared to that of yeast of the vector control.

EXAMPLE 3

Discussion

[Phenotype of MoTR1]

When culturing a knock-out strain in which T-DNA is inserted in At2g25680 (MoTR1-1 and MoTR1-2) is cultured in MGRL water culture solution containing $1.7 \times 10^2$ nM of $MoO_4^{2-}$, Mo concentration in leaves decreased to about ⅓ of that of wild-type strains (FIG. 3). Further, Mo concentration in MoTR1-1 and MoTR1-2 leaves lowered to about ½ of that of the wild-type strain (Col-0) in a strain having the inserted gene as hetero, and to about ¹⁄₁₀ in a strain having the inserted gene as homo (FIG. 4). These results suggest that the mutation by which Mo concentration in leaves decreases in MoTR1 is semi-dominant.

On the other hand, MoTR1-1 and MoTR1-2 did not show any specific phenotypes other than lowering of Mo concentration. When cultured in a water culture solution containing $1.7 \times 10^2$ nM of $MoO_4^{2-}$, growth of MoTR1-1 and MosTR1-2 was not inhibited during nutrition growth phase and genital growth phase. Seeds obtained from MoTR1-1 and MoTR1-2 germinated normally. Further, Mo-deficient sensitivity when cultured in a $MoO_4^{2-}$-free water culture solution, was investigated as well as the nitrogen-deficient sensitivity when cultured in a water culture solution in which $NO_3^-$ concentration is 1/50. There was no significant difference of growth inhibition between MoTR1-1 and MoTR1-2, and a wild-type under these environments.

It has been reported that a wild-type strain (chl2) in which the content of Mo cofactor, a coenzyme containing Mo, is small, show a characteristic phenotype, showing a resistance against perchlorate and sensitivity against tungstate, when the activity of nitrate reductase lowers (nonpatent document 7). Chl2 cultured in a water culture solution containing $1.7 \times 10^2$ nM of $MoO_4^2$, supplemented with 2 mM $KClO_3$ or 0.1 mM $Na_2WO_4$, show these characteristic phenotypes, while no significant difference was observed in these phenotypes even by culturing MoTR1-1 and MoTR1-2, and wild-type strains under these conditions.

The results of these physiological experiments, show that $MoO_4^{2-}$ concentration of the water culture solution necessary for MoTR1 growth is less than $1.7 \times 10^2$ nM, and suggest that a $MoO_4^{2-}$ level more than the necessary level is accumulated in the body of a wild-type. Mo storage mechanism of *Arabidopsis thaliana* is not known, but the Mo concentration in wild-type leaves is proportional to the growth duration under the conditions of the present experiment. The investigation of MoTR1 expression tissues following growth phases, is expected to elucidate the Mo storage mechanism.

[Mo Transport Activity of MoTR1]

MoTR1 was a gene encoding a cell membrane protein (FIG. 5). 2 hypotheses were established for the mechanism by which MoTR1 determines Mo concentration in *Arabidopsis thaliana* leaves. One is a mechanism in which MoTR1 controls directly Mo transport as a transporter. The other is a mechanism in which MoTR1 indirectly controls Mo transport by perceiving Mo concentration change as a sensor, and controlling Mo transport activity of another protein. In the present study, Mo concentration was measured after expressing MoTR1 in yeast. If MoTR1 is a sensor, it is thought that Mo concentration of the cell does not increase unless a signaling mechanism similar to that of *Arabidopsis thaliana*, and a Mo transporter responding to the signal also exist in the yeast. On the other hand, if MoTR1 is a Mo transporter, it can be estimated that as long as a translated product is localized in a cell membrane and has an activity, Mo concentration of the cell is somehow affected. The fact that Mo concentration in yeast in which MoTR1 was expressed increased to 80 times or more than that of a wild-type strains, suggests that MoTR1 is an Mo transporter (FIG. 6).

In order to estimate the property of Mo transport activity of MoTR1, Mo concentration in the cell was calculated roughly. Generally, in a yeast culture solution with an $OD_{600}$ level of about 0.5, about ⅓ mg/ml of cells exists by fresh weight, and it is estimated that the dried weight is about 0.4 mg/ml (Sherman, 2002). In the present estimation, the rate of fresh weight/dried weight of yeast which has been transferred to a medium containing $1.7 \times 10^2$ nM of $MoO_4^{2-}$, and cultured by shaking for 30 min is estimated to follow the previous example, and the difference of fresh weight and dried weight was considered to be the liquid content in the cell. Mo concentration after culture by shaking calculated under this hypothesis was about 250 μM. Therefore, it is estimated that MoTR1 is a transporter having an ability to concentrate Mo against the concentration gradient.

[Expression Tissue of MoTR1 and Expression Induction]

Figure 7:
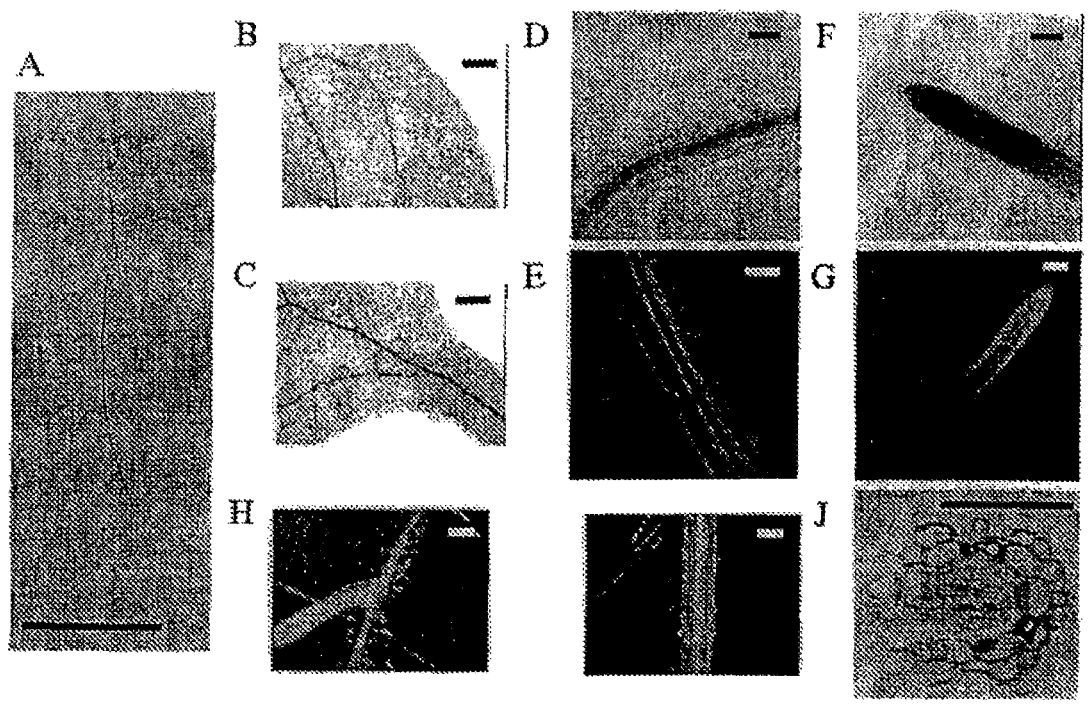

In a transgenic strain in which GUS gene is linked to a promoter region approximately 2.9 kb from the initiation codon of At2g25680, a tissue-specific GUS activity was observed (FIG. 7). Expression pattern in root area is similar to that of nitrate ion transporter AtNRT1.1 which is reported so far (Guo, F. Q., Wang, R., Chen, M. and Crawford, N. M. (2001) The *Arabidopsis* dual-affinity nitrate transporter gene AtNRT1.1 (CHL1) is activated and functions in nascent organ development during vegetative and reproductive growth. Plant Cell 1/3: 1761-1777). As $NO_3^-$ concentration is enhanced in a tissue where AtNRT1.1 is expressed, it is estimated that nitrate reductase activity is increased in these tissues. Nitrate reductase which is responsible for an important reaction of nitrogen metabolic pathway is one of an enzyme containing Mo. Therefore, there is a possibility that MoTR1 is expressed in the same tissue as AtNRT1.1, contributing to nitrogen metabolism by providing Mo to nitrate reductase.

GUS activity in mature root was observed in the pericyle in the root apex part and upper than the region where lateral root is observed, activity was observed in the cortex. Lateral root primordium is formed in the pericycle (Casimiro, I., Beeckman, T., Graham, N., Bhalerao, R., Zhang, H., Casero, P., Sandberg, G. and Bennett, M. J. (2003) Dissecting *Arabidopsis* lateral root development. Trends Plant Sci. 8: 165-171), and it is reported that nitrate reductase is expressed during its formation in the lateral root primordium formation site of chicory (Vuylsteker, C., Prinsen, E., Boutin, J., Onckelen, H. V. and Rambour, S. (1998) Evidence formitrate reductase expression during initiation of lateral roots by NAA in chicory. J. Exp. Bot. 49: 937-944). Moreover, it is shown that $NO_3^-$ concentration of root area dominates lateral root formation in *Arabidopsis thaliana* (Zhang, H. and Forde, B. G. (2000) Regulation of *Arabidopsis* root development by nitrate availability. J. Exp. Bot. 51: 51-59). The change of expression tissue of MoTR1 near the site where lateral root is formed, may suggest that MoTR1 is associated with lateral root formation via nitrate reductase activation by providing Mo. A new phenotype of a mutated strain may be found out by confirming whether there is a change in lateral root formation when MoTR1 is cultured in a water culture solution containing various concentrations of $NO_3$ and $MoO_4^{2-}$.

[Michaelis Constant]

The obtained Michaelis constant is a very small value compared to the one that has been reported for other plant essential element and transporter thereof, suggesting that the molybdenum transporter has a high affinity with molybdenum.

[Growth of *Arabidopsis thaliana* Under Molybdenum-deficient Environment]

As a result of considering *Arabidopsis thaliana* growth under molybdenum-deficient environment, growth of a wild-type strain was suppressed in the absence of molybdenum, while the growth of a mutated strain was significantly suppressed. Therefore, it was suggested that *Arabidopsis thaliana* is weakened against molybdenum deficiency, when a molybdenum transporter does not function normally, and consequently the importance of a molybdenum transporter in a wild-type strain was suggested. Therefore, it was confirmed that the molybdenum of the present invention plays an important role in *Arabidopsis thaliana* growth in an environment with a small amount of molybdenum.

[Mo Concentration of Yeast in which *Oryza sativa* MoTR1 Homologous Gene is Expressed]

By considering Mo transport activity of two types of *Oryza sativa* MoTR1 homologous genes, the increase of Mo concentration in yeast expressing the gene was higher compared to that of yeast of a vector control. Thus, it is thought that a protein encoded by *Oryza sativa* MoTR1 homologous gene has an activity of transporting molybdenum.

On the other hand, as MoTR1 has a homologous domain as that of nitrate ion transporter (Takahashi, H., Noji, M., Hirai, M. Y. and Saito, K. (2003) Molecular regulation of assimilatory sulfur metabolism in plants. Tanpakushitsu Kakusan Koso 48: 2121-2129, in Japanese), there is a possibility that the MoTR1 expression level is controlled depending on nitrate ion concentration in a medium. Sulfur and nitrogen are elements constituting an amino acid, and it has been reported that the rate of sulfur and nitrogen in a plant is controlled by a feedback controlling mechanism, using o-acetylserin, a connection point of each anabolic pathway, as a signaling molecule (Kim, H., Hirai, M. Y., Hayashi, H., Chino, M., Naito, S, and fujiwara, T. (1999) Role of o-acetyl-L-serine in the coordinated regulation of the expression of a soybean seed storage-protein gene by sulfur and nitrogen nutrition. Planta 209: 282-289). Mo is an element contained in nitrate reductase, and the Mo abundance in a plant is a factor determining the nitrogen level that can be used for biosynthesis of amino acid. Therefore, if the expression level of MoTR1 is adjusted according to sulfate ion concentration in the medium, it can be thought that it is a mechanism controlling the sulfur and nitrogen ratio via Mo absorption from soil, which is different from a known feedback mechanism.

MoTR1 expressed in aerial part is estimated to play a role to distribute Mo transported from root via conduit to leaves. Foliar application is effective to Mo deficiency of plant, and it is reported that Mo is translocated via sieve tube (nonpatent document 9). It is estimated that a key to elucidate distribution strategy of Mo in plants can be obtained by investigating expression pattern of MoTR1 during latter nutrition growth phase and genital growth phase.

[Homologous Gene of MoTR1]

Genes having a high homology with the translation region of MoTR1 were searched by each of BLAST, WU-BLAST2, FASTA (website address <<www.arabidopsis.org>>), by using all gene sequences of *Arabidopsis thaliana* (The *Arabidopsis* Genome Initiative, 2000), and there was no gene determined to have a high homology in any of these means. All Mo transporters determined with bacteria or archea were ABC-type transporters (nonpatent document 10), and sequence thereof and MoTR1 have a low homology.

On the other hand, MoTR1 has a homologous domain with nitrate ion transporter (Takahashi, H., Noji, M., Hirai, M. Y. and Saito, K. (2003) Molecular regulation of assimilatory sulfur metabolism in plants. Tanpakushitsu Kakusan Koso 48: 2121-2129, in Japanese). From the sequence analysis of genomic DNA, it is estimated that at least 14 nitrate ion transporters exist in *Arabidopsis thaliana*, and it is thought that these constitute the sulfate ion transporters family. Takahashi et al further classified this family into 5 groups, depending on sequence homology. MoTR1 was considered to belong to Group 5 (Sultr 5). By this classification, Group 5 is constituted from 2 genes which have been designated as At2g25680 (Sultr5; 2) and Atig80310 (Sultr5; 1) in this study. Homology of the genes of this group and those of other groups is lower than homology amount the 4 other groups (nonpatent document 17). There is no report having confirmed the sulfate ion transport activity of the translated product of genes of Group 5.

Therefore, there is a possibility that MoTR1 has a sulfate ion transport activity, in addition to Mo transport activity. On the contrary, other genes belonging to the sulfate ion transporter family, particularly translated products of At1g80310 is also thought to have a Mo transport activity. Further, the sulfate ion transporter family establishes a mechanism to retain sulfate ion concentration at a certain level in a plant, regardless of the outer environment, as transporters having a high affinity and a low affinity against the sulfate ion concentration change in soil collaborate skillfully (nonpatent document 17). Therefore, if At1g80301 is a Mo transporter, there is a possibility that MoTR1 (Sultr 5; 2) and At1g80310 (Sultr 5; 1) are collaborating as a high affinity-type or low affinity-type Mo transporter, by a similar mechanism for Mo absorption and transport.

INDUSTRIAL APPLICABILITY

By using a molybdenum transporter of the present invention, or a molybdenum transporter gene encoding thereof, it may be possible to enhance the production ability by controlling molybdenum absorption of plant, or to control cell activity by introducing it into animal cells, to apply for removing molybdenum from the environment.

The invention claimed is:

1. A method of producing a transgenic plant having a molybdenum transporter activity, wherein the method comprises the steps:
 (a) constructing a recombinant vector comprising a DNA operably linked to a promoter, wherein the DNA is selected from the group consisting of:
  (a1) a DNA encoding a molybdenum transporter consisting of the amino acid sequence shown in SEQ ID NO: 2, 31, 33, or 35;
  (a2) a DNA consisting of the nucleotide sequence shown in SEQ ID NO: 1, 30, 32 or 34;
  (a3) a DNA having at least 95% homology with the nucleotide sequence shown in SEQ ID No: 1, 30, 32 or 34 and which encodes a protein having molybdenum transporter activity; and
 (b) introducing the recombinant vector into a plant cell.

2. A method of removing molybdenum from a molybdenum-containing soil environment comprising growing a transgenic plant produced by the method according to claim 1 in said soil environment.

* * * * *

SEQUENCE LISTING

<160> NUMBER OF SEQ ID NOS: 53

<210> SEQ ID NO 1
<211> LENGTH: 1371
<212> TYPE: DNA
<213> ORGANISM: Arabidopsis thaliana

<400> SEQUENCE: 1

| | | | | | |
|---|---|---|---|---|---|
| atggagtctc | agtctcagag | aggtcaacac | gaaaccccga | acgttctag | gttcaccgga | 60 |
| atgttccata | aactgaaaac | gaatcttgtt | ttccggtcga | agctagccga | aataaacggt | 120 |
| gcaatgggtg | atcttggtac | ttacatacca | atcgtcctcg | ctttaactct | agccaaggat | 180 |
| ttggatttag | gcacaacact | gatattcacc | ggcatataca | acgcgataac | cggagcagtt | 240 |
| tacggtgtcc | ccatgccggt | tcaaccgatg | aaatcgatag | cagccgtggc | gatttcgtct | 300 |
| accgcggaag | atttcggtat | accggagatt | atggctgccg | aatatgtac | cggagggatc | 360 |
| ttgttcgtgt | tggggatctc | tggtttgatg | cagcttgtgt | tcaatataat | cccttttatcg | 420 |
| gttgttagag | ggattcagtt | gtcacaaggc | ttagcttttg | ccatgtctgc | ggttaagtat | 480 |
| ataaggaaag | agcagaattt | ttcgaagtca | agagtgttg | gtgataggcc | atggttaggg | 540 |
| cttgatggtt | tggttttggc | tttggtttgt | gttctgttca | tagttcttgt | gaatggagat | 600 |
| ggtgaagaag | aagaggaaga | ggaagaagga | gatggttcga | aggaagagg | aagatggggt | 660 |
| tcggtgagga | aggttatagc | taacgtgcca | tctgctctgt | tgatattctt | gttgggtgtt | 720 |
| gttttggcat | ttataaggaa | gccgagtatt | gtacatgaca | tcaagtttgg | accgtcaaag | 780 |
| atgaagattg | tgagaataag | ccgaaaagca | tggagaaacg | ggttttttgaa | agggacggtc | 840 |
| ccgcagttac | ctctttctgt | tcttaattct | gttgtggctg | tgtgtaagct | gtcgtatgat | 900 |
| ctgttccccg | agaaggagtt | ctcggctgca | tcggtttcca | tgactgttgg | gctgatgaat | 960 |
| atggtgggat | gttggtttgg | agcaatgcct | acttgtcatg | gagctggtgg | tttagccggg | 1020 |
| cagtataagt | ttggtgggag | gagtggtggg | tgtgtggcac | tgttgggagt | agctaaactg | 1080 |
| gtgctagggt | tggtcttggg | aggttcattg | gtgggtatat | ggagaagtt | tccggttggt | 1140 |
| gtgctcgggg | cattgctact | atttgcaggg | gtagagcttg | caatggcggc | tagagatatg | 1200 |
| aatacaaagg | gagatgcatt | tgtaatgctt | atgtgcacat | cagtctcttt | gggatcaaat | 1260 |
| gctgccatag | gctttgttgc | tggtgatctt | ttgtatgtgg | ttttgtggat | gcggaactac | 1320 |
| gggcgagcga | agccgagcag | ccttcccccg | caatccggtg | aacatgcttg | a | 1371 |

<210> SEQ ID NO 2
<211> LENGTH: 456
<212> TYPE: PRT
<213> ORGANISM: Arabidopsis thaliana

<400> SEQUENCE: 2

Met Glu Ser Gln Ser Gln Arg Gly Gln His Glu Thr Pro Lys Arg Ser
1               5                   10                  15

Arg Phe Thr Gly Met Phe His Lys Leu Lys Thr Asn Leu Val Phe Arg
            20                  25                  30

Ser Lys Leu Ala Glu Ile Asn Gly Ala Met Gly Asp Leu Gly Thr Tyr
        35                  40                  45

Ile Pro Ile Val Leu Ala Leu Thr Leu Ala Lys Asp Leu Asp Leu Gly
    50                  55                  60

-continued

```
Thr Thr Leu Ile Phe Thr Gly Ile Tyr Asn Ala Ile Thr Gly Ala Val
 65                  70                  75                  80

Tyr Gly Val Pro Met Pro Val Gln Pro Met Lys Ser Ile Ala Ala Val
                 85                  90                  95

Ala Ile Ser Ser Thr Ala Glu Asp Phe Gly Ile Pro Glu Ile Met Ala
            100                 105                 110

Ala Gly Ile Cys Thr Gly Gly Ile Leu Phe Val Leu Gly Ile Ser Gly
            115                 120                 125

Leu Met Gln Leu Val Phe Asn Ile Ile Pro Leu Ser Val Val Arg Gly
130                 135                 140

Ile Gln Leu Ser Gln Gly Leu Ala Phe Ala Met Ser Ala Val Lys Tyr
145                 150                 155                 160

Ile Arg Lys Glu Gln Asn Phe Ser Lys Ser Lys Ser Val Gly Asp Arg
                165                 170                 175

Pro Trp Leu Gly Leu Asp Gly Leu Val Leu Ala Leu Val Cys Val Leu
            180                 185                 190

Phe Ile Val Leu Val Asn Gly Asp Gly Glu Glu Glu Glu Glu Glu Glu
            195                 200                 205

Glu Gly Asp Gly Ser Arg Gly Arg Gly Arg Trp Gly Ser Val Arg Lys
210                 215                 220

Val Ile Ala Asn Val Pro Ser Ala Leu Leu Ile Phe Leu Leu Gly Val
225                 230                 235                 240

Val Leu Ala Phe Ile Arg Lys Pro Ser Ile Val His Asp Ile Lys Phe
                245                 250                 255

Gly Pro Ser Lys Met Lys Ile Val Arg Ile Ser Arg Lys Ala Trp Arg
            260                 265                 270

Asn Gly Phe Leu Lys Gly Thr Val Pro Gln Leu Pro Leu Ser Val Leu
            275                 280                 285

Asn Ser Val Val Ala Val Cys Lys Leu Ser Tyr Asp Leu Phe Pro Glu
290                 295                 300

Lys Glu Phe Ser Ala Ala Ser Val Ser Met Thr Val Gly Leu Met Asn
305                 310                 315                 320

Met Val Gly Cys Trp Phe Gly Ala Met Pro Thr Cys His Gly Ala Gly
                325                 330                 335

Gly Leu Ala Gly Gln Tyr Lys Phe Gly Gly Arg Ser Gly Gly Cys Val
            340                 345                 350

Ala Leu Leu Gly Val Ala Lys Leu Val Leu Gly Leu Val Leu Gly Gly
            355                 360                 365

Ser Leu Val Gly Ile Leu Glu Lys Phe Pro Val Gly Val Leu Gly Ala
370                 375                 380

Leu Leu Leu Phe Ala Gly Val Glu Leu Ala Met Ala Ala Arg Asp Met
385                 390                 395                 400

Asn Thr Lys Gly Asp Ala Phe Val Met Leu Met Cys Thr Ser Val Ser
                405                 410                 415

Leu Gly Ser Asn Ala Ala Ile Gly Phe Val Ala Gly Asp Leu Leu Tyr
            420                 425                 430

Val Val Leu Trp Met Arg Asn Tyr Gly Arg Ala Lys Pro Ser Ser Leu
            435                 440                 445

Pro Pro Gln Ser Gly Glu His Ala
450                 455
```

-continued

```
<210> SEQ ID NO 3
<211> LENGTH: 20
<212> TYPE: DNA
<213> ORGANISM: Artificial Sequence
<220> FEATURE:
<223> OTHER INFORMATION: Primer: T28I24 (up stream)

<400> SEQUENCE: 3
gacagagagc ccatttggtg                                              20

<210> SEQ ID NO 4
<211> LENGTH: 20
<212> TYPE: DNA
<213> ORGANISM: Artificial Sequence
<220> FEATURE:
<223> OTHER INFORMATION: Primer: TBI24 (down stream)

<400> SEQUENCE: 4
tcgcttagta tcgcttcgag                                              20

<210> SEQ ID NO 5
<211> LENGTH: 27
<212> TYPE: DNA
<213> ORGANISM: Artificial Sequence
<220> FEATURE:
<223> OTHER INFORMATION: Primer: F27A10 (up stream)

<400> SEQUENCE: 5
tcatacagct ttaataccaa tcagtaa                                      27

<210> SEQ ID NO 6
<211> LENGTH: 20
<212> TYPE: DNA
<213> ORGANISM: Artificial Sequence
<220> FEATURE:
<223> OTHER INFORMATION: F27A10 (down stream)

<400> SEQUENCE: 6
cagtttgtgt acgggatgaa                                              20

<210> SEQ ID NO 7
<211> LENGTH: 20
<212> TYPE: DNA
<213> ORGANISM: Artificial Sequence
<220> FEATURE:
<223> OTHER INFORMATION: Primer: F13B15_01 (up stream)

<400> SEQUENCE: 7
caatttccga cggttgaata                                              20

<210> SEQ ID NO 8
<211> LENGTH: 21
<212> TYPE: DNA
<213> ORGANISM: Artificial Sequence
<220> FEATURE:
<223> OTHER INFORMATION: Primer: F13B15_01 (down stream)

<400> SEQUENCE: 8
ccatcccgcg acttctatat g                                            21

<210> SEQ ID NO 9
<211> LENGTH: 27
<212> TYPE: DNA
<213> ORGANISM: Artificial Sequence
<220> FEATURE:
<223> OTHER INFORMATION: Primer: F13B15_02 (up stream)
```

```
<400> SEQUENCE: 9
ccaaactttt attttctcca ctaacaa                                              27

<210> SEQ ID NO 10
<211> LENGTH: 20
<212> TYPE: DNA
<213> ORGANISM: Artificial Sequence
<220> FEATURE:
<223> OTHER INFORMATION: Primer: F13B15_02 (down stream)

<400> SEQUENCE: 10
cgatgtttgt cactgctctg                                                       20

<210> SEQ ID NO 11
<211> LENGTH: 20
<212> TYPE: DNA
<213> ORGANISM: Artificial Sequence
<220> FEATURE:
<223> OTHER INFORMATION: Primer: F3N11_01 (up stream)

<400> SEQUENCE: 11
attccggtga acctagaacg                                                       20

<210> SEQ ID NO 12
<211> LENGTH: 21
<212> TYPE: DNA
<213> ORGANISM: Artificial Sequence
<220> FEATURE:
<223> OTHER INFORMATION: Primer: F3N11_01 (down stream)

<400> SEQUENCE: 12
tcagatactg tcgccatcaa g                                                     21

<210> SEQ ID NO 13
<211> LENGTH: 20
<212> TYPE: DNA
<213> ORGANISM: Artificial Sequence
<220> FEATURE:
<223> OTHER INFORMATION: Primer: F3N11_02 (up stream)

<400> SEQUENCE: 13
aatgcacgca cccttctact                                                       20

<210> SEQ ID NO 14
<211> LENGTH: 20
<212> TYPE: DNA
<213> ORGANISM: Artificial Sequence
<220> FEATURE:
<223> OTHER INFORMATION: Primer: F3N11_02 (down stream)

<400> SEQUENCE: 14
ggttgataac ttgcggcttt                                                       20

<210> SEQ ID NO 15
<211> LENGTH: 21
<212> TYPE: DNA
<213> ORGANISM: Artificial Sequence
<220> FEATURE:
<223> OTHER INFORMATION: Primer: F17H15 (up stream)

<400> SEQUENCE: 15
aggcaatgtg cttatgtcaa a                                                     21
```

```
<210> SEQ ID NO 16
<211> LENGTH: 21
<212> TYPE: DNA
<213> ORGANISM: Artificial Sequence
<220> FEATURE:
<223> OTHER INFORMATION: Primer: F17H15 (down stream)

<400> SEQUENCE: 16
cctcatattt ggattgggtt g                                              21

<210> SEQ ID NO 17
<211> LENGTH: 20
<212> TYPE: DNA
<213> ORGANISM: Artificial Sequence
<220> FEATURE:
<223> OTHER INFORMATION: Primer: T19L18 (up stream)

<400> SEQUENCE: 17
tttcgagttt ggacattgga                                                20

<210> SEQ ID NO 18
<211> LENGTH: 22
<212> TYPE: DNA
<213> ORGANISM: Artificial Sequence
<220> FEATURE:
<223> OTHER INFORMATION: Primer: T19L18 (down stream)

<400> SEQUENCE: 18
gctttggtgc aaattaatac cc                                             22

<210> SEQ ID NO 19
<211> LENGTH: 22
<212> TYPE: DNA
<213> ORGANISM: Artificial Sequence
<220> FEATURE:
<223> OTHER INFORMATION: Primer: SALK T-DNA (LBb1)

<400> SEQUENCE: 19
gatggcccac tacgtgaacc at                                             22

<210> SEQ ID NO 20
<211> LENGTH: 21
<212> TYPE: DNA
<213> ORGANISM: Artificial Sequence
<220> FEATURE:
<223> OTHER INFORMATION: Primer: SALK T-DNA (RB)

<400> SEQUENCE: 20
tagtgacctt aggcgacttt t                                              21

<210> SEQ ID NO 21
<211> LENGTH: 22
<212> TYPE: DNA
<213> ORGANISM: Artificial Sequence
<220> FEATURE:
<223> OTHER INFORMATION: Primer: SALK_118311(LP1)

<400> SEQUENCE: 21
tcggggaaca gatcatacga ca                                             22

<210> SEQ ID NO 22
<211> LENGTH: 22
<212> TYPE: DNA
<213> ORGANISM: Artificial Sequence
<220> FEATURE:
<223> OTHER INFORMATION: Primer: SALK_118311(RP1)
```

```
<400> SEQUENCE: 22
ccgaaacgtt ctaggttcac cg                                          22

<210> SEQ ID NO 23
<211> LENGTH: 21
<212> TYPE: DNA
<213> ORGANISM: Artificial Sequence
<220> FEATURE:
<223> OTHER INFORMATION: Primer: SALK_069683(LP2)

<400> SEQUENCE: 23
cgcgttgtat atgccggtga a                                           21

<210> SEQ ID NO 24
<211> LENGTH: 25
<212> TYPE: DNA
<213> ORGANISM: Artificial Sequence
<220> FEATURE:
<223> OTHER INFORMATION: Primer: SALK_069683(RP2)

<400> SEQUENCE: 24
cgaatgttca agactaccgg aaaca                                       25

<210> SEQ ID NO 25
<211> LENGTH: 40
<212> TYPE: DNA
<213> ORGANISM: Aridopsis thaliana

<400> SEQUENCE: 25
acgcgtcgac gaattcacaa tggagtctca gtctcagaga                       40

<210> SEQ ID NO 26
<211> LENGTH: 29
<212> TYPE: DNA
<213> ORGANISM: Arabidopsis thaliana

<400> SEQUENCE: 26
ccgctcgagt caagcatgtt caccggatt                                   29

<210> SEQ ID NO 27
<211> LENGTH: 35
<212> TYPE: DNA
<213> ORGANISM: Arabidopsis thaliana

<400> SEQUENCE: 27
cgggatccgc ctcctccagc atgttcaccg gattg                            35

<210> SEQ ID NO 28
<211> LENGTH: 26
<212> TYPE: DNA
<213> ORGANISM: Arabidopsis thaliana

<400> SEQUENCE: 28
cgggatcctt tcgaaatgag atccga                                      26

<210> SEQ ID NO 29
<211> LENGTH: 22
<212> TYPE: DNA
<213> ORGANISM: Arabidopsis thaliana

<400> SEQUENCE: 29
gactccatgg tttctgtttt gt                                          22
```

<210> SEQ ID NO 30
<211> LENGTH: 1395
<212> TYPE: DNA
<213> ORGANISM: Arabidopsis thaliana

<400> SEQUENCE: 30

```
atggagacaa ctacaactcc tctgctcccc ggtgatcgca gcagatgcgg gtggctccgt      60
cgccgtctcc gcctcaaaaa ccctctttct tctgaactct ccggcgctgt cggtgatctc     120
ggcaccttca tccccatcgt ccttacacta actctagtct ccaatcttga tctctccacc     180
actctcatct tcactggttt ctacaacatc gccaccggtc tcctctttga catccctatg     240
cccgtccagc ccatgaaatc catcgccgct gtcgctgtct ccgaatcccc gcatctaact     300
ccttctcaga ttgccgccgc tggtgcatcc actgccgcca cgctcctcct ccttggcgcc     360
accggagcta tgtctttcct ctacaacatc atccctctcc cagttgtacg cggcgtccag     420
ctttctcaag tcttcagtt cgccttcacc gccatcaaat acgtcaggtt taattacgat     480
actgccactc tcaaaccctc ttcttctcct cgtatttggc ttggcctcga cggccttatc     540
ttggctctag ctgctctgct cttcatcatt ttgtccaccg gctctggcaa cgacagagaa     600
gctgaagatg gagatctcgc cgagacttcc agcaacgaaa gccagtctcg ccggaggaga     660
ctgcgtcttc tgtcttcgat ccatctgcg ctgatcgtgt tcgcactcgg gttagtgctc     720
tgtttcatac gtgatccatc cattttcaaa gaccttaaat tcggtccctc gaagttccac     780
attctgagaa tcagttggga tgattggaaa atcgggtttc tgagggcggc gattcctcag     840
attccactct ctgtactgaa ctcagtgatc gcagtttgta aattatccaa tgacttgttt     900
gacaaggaac tctctgcgac tacagtctcc atcagcgttg gggtgatgaa cttaataggg     960
tgctggtttg gcgctatgcc cgtctgtcac ggtgctggtg ggttagctgg tcagtatcgg    1020
tttggggcaa ggagtggatt atccgttatt tttctcggaa tcgggaaact gattgtgggt    1080
ctggtgtttg gaaactcctt tgtaaggatt ctgagtcagt ttccgattgg aattttaggg    1140
gttctgttgc tattcgcggg aatcgaactg gcaatggctt ccaaagacat gaactccaaa    1200
gaagattcct tcatcatgct ggtctgcgcc gctgtgtcga tgactggctc gagtgccgcc    1260
ttaggatttg gttgtggagt tgttctttac ttgttactga agctaagaac gttagactgt    1320
tcttcagtaa ctctgttttc ccggtcaagt gatgagtcgc aggtcgattc cgaagccgct    1380
cctcgtgatg tctaa                                                    1395
```

<210> SEQ ID NO 31
<211> LENGTH: 464
<212> TYPE: PRT
<213> ORGANISM: Arabidopsis thaliana

<400> SEQUENCE: 31

```
Met Glu Thr Thr Thr Thr Pro Leu Leu Pro Gly Asp Arg Ser Arg Cys
1               5                   10                  15

Gly Trp Leu Arg Arg Arg Leu Arg Leu Lys Asn Pro Leu Ser Ser Glu
            20                  25                  30

Leu Ser Gly Ala Val Gly Asp Leu Gly Thr Phe Ile Pro Ile Val Leu
        35                  40                  45

Thr Leu Thr Leu Val Ser Asn Leu Asp Leu Ser Thr Thr Leu Ile Phe
    50                  55                  60

Thr Gly Phe Tyr Asn Ile Ala Thr Gly Leu Leu Phe Asp Ile Pro Met
65                  70                  75                  80
```

```
Pro Val Gln Pro Met Lys Ser Ile Ala Ala Val Ala Val Ser Glu Ser
                85                  90                  95

Pro His Leu Thr Pro Ser Gln Ile Ala Ala Gly Ala Ser Thr Ala
            100                 105                 110

Ala Thr Leu Leu Leu Gly Ala Thr Gly Ala Met Ser Phe Leu Tyr
            115                 120                 125

Asn Ile Ile Pro Leu Pro Val Val Arg Gly Val Gln Leu Ser Gln Gly
130                 135                 140

Leu Gln Phe Ala Phe Thr Ala Ile Lys Tyr Val Arg Phe Asn Tyr Asp
145                 150                 155                 160

Thr Ala Thr Leu Lys Pro Ser Ser Pro Arg Ile Trp Leu Gly Leu
                165                 170                 175

Asp Gly Leu Ile Leu Ala Leu Ala Ala Leu Leu Phe Ile Ile Leu Ser
            180                 185                 190

Thr Gly Ser Gly Asn Asp Arg Glu Ala Glu Asp Gly Asp Leu Ala Glu
            195                 200                 205

Thr Ser Ser Asn Glu Ser Gln Ser Arg Arg Arg Leu Arg Leu Leu
210                 215                 220

Ser Ser Ile Pro Ser Ala Leu Ile Val Phe Ala Leu Gly Leu Val Leu
225                 230                 235                 240

Cys Phe Ile Arg Asp Pro Ser Ile Phe Lys Asp Leu Lys Phe Gly Pro
                245                 250                 255

Ser Lys Phe His Ile Leu Arg Ile Ser Trp Asp Asp Trp Lys Ile Gly
            260                 265                 270

Phe Leu Arg Ala Ala Ile Pro Gln Ile Pro Leu Ser Val Leu Asn Ser
            275                 280                 285

Val Ile Ala Val Cys Lys Leu Ser Asn Asp Leu Phe Asp Lys Glu Leu
            290                 295                 300

Ser Ala Thr Thr Val Ser Ile Ser Val Gly Val Met Asn Leu Ile Gly
305                 310                 315                 320

Cys Trp Phe Gly Ala Met Pro Val Cys His Gly Ala Gly Gly Leu Ala
                325                 330                 335

Gly Gln Tyr Arg Phe Gly Ala Arg Ser Gly Leu Ser Val Ile Phe Leu
            340                 345                 350

Gly Ile Gly Lys Leu Ile Val Gly Leu Val Phe Gly Asn Ser Phe Val
            355                 360                 365

Arg Ile Leu Ser Gln Phe Pro Ile Gly Ile Leu Gly Val Leu Leu Leu
            370                 375                 380

Phe Ala Gly Ile Glu Leu Ala Met Ala Ser Lys Asp Met Asn Ser Lys
385                 390                 395                 400

Glu Asp Ser Phe Ile Met Leu Val Cys Ala Ala Val Ser Met Thr Gly
                405                 410                 415

Ser Ser Ala Ala Leu Gly Phe Gly Cys Gly Val Val Leu Tyr Leu Leu
            420                 425                 430

Leu Lys Leu Arg Thr Leu Asp Cys Ser Ser Val Thr Leu Phe Ser Arg
435                 440                 445

Ser Ser Asp Glu Ser Gln Val Asp Ser Glu Ala Ala Pro Arg Asp Val
            450                 455                 460

<210> SEQ ID NO 32
<211> LENGTH: 1368
<212> TYPE: DNA
<213> ORGANISM: Oryza sativa
```

<400> SEQUENCE: 32

```
atggccggcg tgggcgtggt agtagatccg gaggcggtgg cggcggtgg agatggaggt      60
ggagatgggc ggatgaagga agggttggcg cggcgggcgg tggaaaacct gaggttccgg    120
tcggtgtggg gcgaggtgaa cggcgccatg ggcgacctcg gacgtacat ccccatcgtg     180
ctgtcgctgg cgctgtcccg gcagctggac ctcggcacca ccctcgtctt caccggcatc   240
tacaacgcca tcaccggcct cctctacggc gtccccatgc ccgtccagcc catgaagtcc   300
atcgccgccg ccgccctcgc cgaccccctcc ttcgccatcc ggagatcat ggccgccggc   360
atcctcaccg ccgccttcgt cctcttcctc ggcctcaccc gcctcatgga cctcgtctac   420
cgcttcgtcc cgctctccgt cgtgcgtggc atccagctcg cccagggcct caacttcgcc   480
atggccgccg tcaagtacat acgctacgag caggacttgg gcaagggcaa gtccctcggg   540
cggcgcccct gggtgggcct cgacggcctc gtgctcgcca tcgcggcggt ctgcttcatc   600
gtgctcgtca acggggccgg agaagagcag gagcagcgtc agcagcagca gcagcagcaa   660
cagtggtggc gtcgtcggtt gggttccgtt ccttcggctg tggtggtgtt cgtggtgggc   720
gttgcgttcg cggtggcgcg tcacccagcg gcggtgaggg agctgcgcgc tgggccgtcg   780
cggatgcggg tggtgcacat ctctcgggag gcgtggaagc aagggttcat caagggcgcg   840
ctgccgcaga tcccgctgtc ggtgctcaac tcggtggtgg cggtgtgcaa gctgacgcgc   900
gacctgttcc ggagcggaa ggagtcgccg acgtcggtgt cggtgacgat gggagccatg   960
aacctggtgg ggtgctggtt cggcgccatg ccgtgctgcc acggcgcggg agggctggcg  1020
gggcagtaca agttcggggg gaggagcggc gggtgcgtgg cggcgctggg cgtgctgaag  1080
ctggcgctgg gcctgctgct gggcggctcc atgctgcgtg tcctcgtcca gttccccgtc  1140
ggtcttctcg gcgcgctgct gctgttcgcc ggagtggagc tcgcggcggc ggcgagggac  1200
atgtccacga gggcggaggc gttcgtgatg ctgctgtgca cggcggtgtc gctggtgggc  1260
tccagcgccg cgctcggctt cctctgcggg atgctcgccc acgcccttct ctacctcagg  1320
gcctgcgcgc tcagggaacg catcgtctca tctcaaacgg atttgtaa              1368
```

<210> SEQ ID NO 33
<211> LENGTH: 455
<212> TYPE: PRT
<213> ORGANISM: Oryza sativa

<400> SEQUENCE: 33

```
Met Ala Gly Val Gly Val Val Asp Pro Glu Ala Val Gly Gly Gly Gly
  1               5                  10                  15

Gly Asp Gly Gly Gly Asp Gly Arg Met Lys Glu Gly Leu Ala Arg Arg
             20                  25                  30

Ala Val Glu Asn Leu Arg Phe Arg Ser Val Trp Gly Glu Val Asn Gly
         35                  40                  45

Ala Met Gly Asp Leu Gly Thr Tyr Ile Pro Ile Val Leu Ser Leu Ala
     50                  55                  60

Leu Ser Arg Gln Leu Asp Leu Gly Thr Thr Leu Val Phe Thr Gly Ile
 65                  70                  75                  80

Tyr Asn Ala Ile Thr Gly Leu Leu Tyr Gly Val Pro Met Pro Val Gln
                 85                  90                  95

Pro Met Lys Ser Ile Ala Ala Ala Ala Leu Ala Asp Pro Ser Phe Ala
            100                 105                 110

Ile Pro Glu Ile Met Ala Ala Gly Ile Leu Thr Ala Ala Phe Val Leu
        115                 120                 125
```

```
Phe Leu Gly Leu Thr Arg Leu Met Asp Leu Val Tyr Arg Phe Val Pro
    130                 135                 140

Leu Ser Val Val Arg Gly Ile Gln Leu Ala Gln Gly Leu Asn Phe Ala
145                 150                 155                 160

Met Ala Ala Val Lys Tyr Ile Arg Tyr Glu Gln Asp Leu Gly Lys Gly
                165                 170                 175

Lys Ser Leu Gly Arg Arg Pro Trp Val Gly Leu Asp Gly Leu Val Leu
            180                 185                 190

Ala Ile Ala Ala Val Cys Phe Ile Val Leu Val Asn Gly Ala Gly Glu
        195                 200                 205

Glu Gln Glu Gln Arg Gln Gln Gln Gln Gln Gln Gln Gln Trp Trp Arg
210                 215                 220

Arg Arg Leu Gly Ser Val Pro Ser Ala Val Val Phe Val Val Gly
225                 230                 235                 240

Val Ala Phe Ala Val Ala Arg His Pro Ala Ala Val Arg Glu Leu Arg
                245                 250                 255

Ala Gly Pro Ser Arg Met Arg Val Val His Ile Ser Arg Glu Ala Trp
            260                 265                 270

Lys Gln Gly Phe Ile Lys Gly Ala Leu Pro Gln Ile Pro Leu Ser Val
        275                 280                 285

Leu Asn Ser Val Val Ala Val Cys Lys Leu Thr Arg Asp Leu Phe Pro
    290                 295                 300

Glu Arg Lys Glu Ser Pro Thr Ser Val Ser Val Thr Met Gly Ala Met
305                 310                 315                 320

Asn Leu Val Gly Cys Trp Phe Gly Ala Met Pro Cys Cys His Gly Ala
                325                 330                 335

Gly Gly Leu Ala Gly Gln Tyr Lys Phe Gly Gly Arg Ser Gly Gly Cys
            340                 345                 350

Val Ala Ala Leu Gly Val Leu Lys Leu Ala Leu Gly Leu Leu Gly
        355                 360                 365

Gly Ser Met Leu Arg Val Leu Val Gln Phe Pro Val Gly Leu Leu Gly
    370                 375                 380

Ala Leu Leu Leu Phe Ala Gly Val Glu Leu Ala Ala Ala Arg Asp
385                 390                 395                 400

Met Ser Thr Arg Ala Glu Ala Phe Val Met Leu Leu Cys Thr Ala Val
                405                 410                 415

Ser Leu Val Gly Ser Ser Ala Ala Leu Gly Phe Leu Cys Gly Met Leu
            420                 425                 430

Ala His Ala Leu Leu Tyr Leu Arg Ala Cys Ala Leu Arg Glu Arg Ile
        435                 440                 445

Val Ser Ser Gln Thr Asp Leu
    450                 455

<210> SEQ ID NO 34
<211> LENGTH: 1392
<212> TYPE: DNA
<213> ORGANISM: Oryza sativa

<400> SEQUENCE: 34
atggcatcct ccgccggcga cccgctcctc tccggcgagg ccggcgacgg ccgccgcagg      60
ttcgtcccgt ccaccatacg gctcaagacg tcggtgtggt cggagctggg cggcgcggtg     120
ggcgatctgg gcacctacat ccccatcgtg ctggcgctgt cgctcgcgtc ccacctcgac     180
ctcggcacca cgctcatctt caccgcgctc tacaacttcg ccaccgggct cctcttcggc     240
```

-continued

```
atccccatgc cgtccagcc catgaagtcc atcgccgccg tcgcgctctc ctccgcgcac    300
ctcaccatcc cgcagatcat gtccgctggc ctcgccgtcg ccgccatcct cctcttcctc    360
ggcgtcaccg gcctcatgac caccctctac cgcctcctcc cgctccccgt cgtgcgcggc    420
gtccagctct cgcagggcct ctccttcgcc ttcaccgccg tcaagtacat ccgctacgtg    480
caggacttct cccgttcctc ctctgcttcc acctccgtgc cgcgccccct cctcggcctc    540
gacggccttg tcctcgcgct cgccgcgcta ctgttcataa tcctcgccac cggctccggc    600
gacgacgagg acgtcaacag ggacggcacg agccgtcgcc gtcgctcctg cagccgcgtc    660
ccggcggcgc taatcgtgtt cgcgctcggc ttggtgctct gcttcgttcg tgatccgtcc    720
atcctgcagg atctccgctt tgggccggcg ccgttggggc tggtcaagat aacctgggac    780
gatttcaaga tcgggttctg ggagggcgcc gtgccgcagc tcccgctgtc cgtgctgaac    840
tcggtgatcg ccgtgtgcaa gctgtcgtcg gacctgttcc cggaacgggc cgagctctcg    900
ccggcgcggg tgtcggtgag cgtggggctc atgaatttcg tggggtgctg gttcggcgcc    960
atgccgtgct gccacggcgc gggcgggctg gcggggcagt accggttcgg cggccggacc   1020
ggcgcgtccg tggtgttcct ggccatcggc aagctggcgc tcgggctggt gttcggcaac   1080
tcgttcgtga cgatcctggg gcagttcccg atcgggatac tgggcgtcat gctgctcttc   1140
tccgggatcg agctcgccat ggcgtcgcgc gacatgggga gcaagcagga gtcgttcgtc   1200
atgctggtct gcgccggcgt gtcgctcaca ggctcgagcg ccgcgctggg cttcatctcc   1260
ggaatcgtgc tgtacctgtt gctacgcctg agggatttgg agtgggatat cagaggactg   1320
ctcggtcgct gggccgcggg acggcggcaa tcgaccaacg aggccaatga agatggggct   1380
ggagatgctt ga                                                       1392
```

<210> SEQ ID NO 35
<211> LENGTH: 463
<212> TYPE: PRT
<213> ORGANISM: Oryza sativa

<400> SEQUENCE: 35

```
Met Ala Ser Ser Ala Gly Asp Pro Leu Leu Ser Gly Glu Ala Gly Asp
1               5                   10                  15

Gly Arg Arg Arg Phe Val Pro Ser Thr Ile Arg Leu Lys Thr Ser Val
                20                  25                  30

Trp Ser Glu Leu Gly Gly Ala Val Gly Asp Leu Gly Thr Tyr Ile Pro
            35                  40                  45

Ile Val Leu Ala Leu Ser Leu Ala Ser His Leu Asp Leu Gly Thr Thr
        50                  55                  60

Leu Ile Phe Thr Ala Leu Tyr Asn Phe Ala Thr Gly Leu Leu Phe Gly
65                  70                  75                  80

Ile Pro Met Pro Val Gln Pro Met Lys Ser Ile Ala Ala Val Ala Leu
                85                  90                  95

Ser Ser Ala His Leu Thr Ile Pro Gln Ile Met Ser Ala Gly Leu Ala
                100                 105                 110

Val Ala Ala Ile Leu Leu Phe Leu Gly Val Thr Gly Leu Met Thr Thr
            115                 120                 125

Leu Tyr Arg Leu Leu Pro Leu Pro Val Val Arg Gly Val Gln Leu Ser
        130                 135                 140

Gln Gly Leu Ser Phe Ala Phe Thr Ala Val Lys Tyr Ile Arg Tyr Val
145                 150                 155                 160
```

```
Gln Asp Phe Ser Arg Ser Ser Ala Ser Thr Ser Val Pro Arg Pro
            165                 170                 175

Leu Leu Gly Leu Asp Gly Leu Val Leu Ala Leu Ala Ala Leu Leu Phe
        180                 185                 190

Ile Ile Leu Ala Thr Gly Ser Gly Asp Glu Asp Val Asn Arg Asp
            195                 200                 205

Gly Thr Ser Arg Arg Arg Ser Cys Ser Arg Val Pro Ala Ala Leu
    210                 215                 220

Ile Val Phe Ala Leu Gly Leu Val Leu Cys Phe Val Arg Asp Pro Ser
225                 230                 235                 240

Ile Leu Gln Asp Leu Arg Phe Gly Pro Ala Pro Leu Gly Leu Val Lys
                245                 250                 255

Ile Thr Trp Asp Asp Phe Lys Ile Gly Phe Trp Glu Gly Ala Val Pro
            260                 265                 270

Gln Leu Pro Leu Ser Val Leu Asn Ser Val Ile Ala Val Cys Lys Leu
        275                 280                 285

Ser Ser Asp Leu Phe Pro Glu Arg Ala Glu Leu Ser Pro Ala Arg Val
    290                 295                 300

Ser Val Ser Val Gly Leu Met Asn Phe Val Gly Cys Trp Phe Gly Ala
305                 310                 315                 320

Met Pro Cys Cys His Gly Ala Gly Gly Leu Ala Gly Gln Tyr Arg Phe
                325                 330                 335

Gly Gly Arg Thr Gly Ala Ser Val Val Phe Leu Ala Ile Gly Lys Leu
            340                 345                 350

Ala Leu Gly Leu Val Phe Gly Asn Ser Phe Val Thr Ile Leu Gly Gln
        355                 360                 365

Phe Pro Ile Gly Ile Leu Gly Val Met Leu Leu Phe Ser Gly Ile Glu
    370                 375                 380

Leu Ala Met Ala Ser Arg Asp Met Gly Ser Lys Gln Glu Ser Phe Val
385                 390                 395                 400

Met Leu Val Cys Ala Gly Val Ser Leu Thr Gly Ser Ser Ala Ala Leu
                405                 410                 415

Gly Phe Ile Ser Gly Ile Val Leu Tyr Leu Leu Arg Leu Arg Asp
            420                 425                 430

Leu Glu Trp Asp Ile Arg Gly Leu Leu Gly Arg Trp Ala Ala Gly Arg
        435                 440                 445

Arg Gln Ser Thr Asn Glu Ala Asn Glu Asp Gly Ala Gly Asp Ala
    450                 455                 460

<210> SEQ ID NO 36
<211> LENGTH: 1614
<212> TYPE: DNA
<213> ORGANISM: Brassica napus

<400> SEQUENCE: 36
tatcatggag acaacgacca ctcctcttct ccccgaccga tgcgggtggc tccgccgtcg     60
tctccgcctc aagaaccctc tttcctctga actctccggc cgtcggtg atcttggcac      120 cttcatcccc atcgtcctga ccctgactct cgtctccaat ctcgatctct ccgccactct    180
catcttcact ggattctaca acatcgccac tggcctcctc ttcgacatcc ccatgcccgt    240
ccagcccatg aaatccatcg ccgccgtcgc cgtctccgag accccgcatc tcactccttc    300
tcagatcgcc gccgccggag catccactgc ggcaacgccc cttcctcctcg cgccacggg    360 agccatgtct ttcctctaca acctcatccc tctcccggtg gtaagaggcg tccagctttc    420
```

```
tcaggggctt cagttcgcct tcaccgccat caaatacgtg aggtatgact acgacactgc    480
cactctcaag ccctcttctt ctccccgttc ctggctcggc ctcgacggcc ttatcttggc    540
tcttgctgct cttctcttca tcattttgtc caccggctcc ggcaccgaca gagactgcgc    600
cggagatgga gattttgcgg agagttcccc cagcaacgaa acgcaatctc gccggaggag    660
actgcgtctt ctctcttcga ttccatctgc gctaatcgtg ttctttgtgg ggttagtgct    720
ctgtttcata cgcgatcctt ccattttcaa agaccttaaa tttggtccat cgaagttcaa    780
gatcctgaaa atcacttggg aggattggaa gatcgggttt gtaagggcgg cgattcctca    840
gattccactc tctgtgctca actctgtgat cgccgtctgt aaattatcca atgacttgtt    900
cgacaaggaa ctatcagcta ctacagtctc cgtaagcgtt ggagtgatga acttaatagg    960
gtgctggttt ggcgcaatgc cggtttgtca cggtgcgggt gggttagctg gcagtatcg   1020 tttcggcgcg aggagtggtt tgtcggttgt ctttctcgga gtcgggaaac tgattgtggg   1080
tttggtgttt gggaactcgt tgtgaggat tctgagccag tttccgatcg aatactggg    1140 ggttctcttg ctgttcgcag ggatcgaact tgccatggct ccaaagata tgaacacgaa   1200 ggaagattcg tttatcatgc tggtctgcgc tgctgtatca atgacaggct caagcgcagc   1260
cctggggttt gggtgtggag ttgttcttta cttgctactg aagctaagaa cgctagactc   1320
ttccgaaaca gcttctcatg tggcctaact taacctttga ggtctgaata ttcaaaattt   1380
gatgtcagcc aattcgtctt tctctcagtt gctggctcag cctcaattca accttagctc   1440
cttgtgtttg caggttggaa cccttatcgc tctgttttta cgcggtccct tgattttta   1500 attccaagag tgtattttgt ttcgattgcg caaagaatgt taaacccta accaatatgt    1560 taatataata aaagtgtata agttatgaa tctttaaact aaaaaaaaaa aaaa   1614
```

<210> SEQ ID NO 37
<211> LENGTH: 447
<212> TYPE: PRT
<213> ORGANISM: Brassica napus

<400> SEQUENCE: 37

```
Met Glu Thr Thr Thr Thr Pro Leu Leu Pro Asp Arg Cys Gly Trp Leu
1               5                   10                  15

Arg Arg Arg Leu Arg Leu Lys Asn Pro Leu Ser Ser Glu Leu Ser Gly
            20                  25                  30

Ala Val Gly Asp Leu Gly Thr Phe Ile Pro Ile Val Leu Thr Leu Thr
        35                  40                  45

Leu Val Ser Asn Leu Asp Leu Ser Ala Thr Leu Ile Phe Thr Gly Phe
    50                  55                  60

Tyr Asn Ile Ala Thr Gly Leu Leu Phe Asp Ile Pro Met Pro Val Gln
65                  70                  75                  80

Pro Met Lys Ser Ile Ala Ala Val Ala Val Ser Glu Thr Pro His Leu
                85                  90                  95

Thr Pro Ser Gln Ile Ala Ala Gly Ala Ser Thr Ala Ala Thr Pro
            100                 105                 110

Leu Leu Leu Gly Ala Thr Gly Ala Met Ser Phe Leu Tyr Asn Leu Ile
        115                 120                 125

Pro Leu Pro Val Val Arg Gly Val Gln Leu Ser Gln Gly Leu Gln Phe
    130                 135                 140

Ala Phe Thr Ala Ile Lys Tyr Val Arg Tyr Asp Tyr Asp Thr Ala Thr
145                 150                 155                 160
```

```
Leu Lys Pro Ser Ser Pro Arg Ser Trp Leu Gly Leu Asp Gly Leu
            165                 170                 175
Ile Leu Ala Leu Ala Ala Leu Leu Phe Ile Ile Leu Ser Thr Gly Ser
        180                 185                 190
Gly Thr Asp Arg Asp Cys Ala Gly Asp Gly Phe Ala Glu Ser Ser
            195                 200                 205
Pro Ser Asn Glu Thr Gln Ser Arg Arg Arg Leu Arg Leu Leu Ser
        210                 215                 220
Ser Ile Pro Ser Ala Leu Ile Val Phe Phe Val Gly Leu Val Leu Cys
225                 230                 235                 240
Phe Ile Arg Asp Pro Ser Ile Phe Lys Asp Leu Lys Phe Gly Pro Ser
                245                 250                 255
Lys Phe Lys Ile Leu Lys Ile Thr Trp Glu Asp Trp Lys Ile Gly Phe
            260                 265                 270
Val Arg Ala Ala Ile Pro Gln Ile Pro Leu Ser Val Leu Asn Ser Val
        275                 280                 285
Ile Ala Val Cys Lys Leu Ser Asn Asp Leu Phe Asp Lys Glu Leu Ser
290                 295                 300
Ala Thr Thr Val Ser Val Ser Val Gly Val Met Asn Leu Ile Gly Cys
305                 310                 315                 320
Trp Phe Gly Ala Met Pro Val Cys His Gly Ala Gly Leu Ala Gly
                325                 330                 335
Gln Tyr Arg Phe Gly Ala Arg Ser Gly Leu Ser Val Val Phe Leu Gly
            340                 345                 350
Val Gly Lys Leu Ile Val Gly Leu Val Phe Gly Asn Ser Phe Val Arg
        355                 360                 365
Ile Leu Ser Gln Phe Pro Ile Gly Ile Leu Gly Val Leu Leu Leu Phe
    370                 375                 380
Ala Gly Ile Glu Leu Ala Met Ala Ser Lys Asp Met Asn Thr Lys Glu
385                 390                 395                 400
Asp Ser Phe Ile Met Leu Val Cys Ala Ala Val Ser Met Thr Gly Ser
                405                 410                 415
Ser Ala Ala Leu Gly Phe Gly Cys Gly Val Val Leu Tyr Leu Leu
            420                 425                 430
Lys Leu Arg Thr Leu Asp Ser Ser Glu Thr Ala Ser His Val Ala
        435                 440                 445

<210> SEQ ID NO 38
<211> LENGTH: 482
<212> TYPE: DNA
<213> ORGANISM: Hordeum vulgare
<220> FEATURE:
<221> NAME/KEY: misc_feature
<222> LOCATION: (389)..(389)
<223> OTHER INFORMATION: n is a, c, g, or t

<400> SEQUENCE: 38
acccatttct atactcagtt cagctcccac ccacagcaat aggactctgc tgtcgtgcag      60
ccagccatgg catcctccgc cggcgacccg ctgctcccgg cgagccgca ccggcggagt      120
ttcctgccgc cgtccatccg gctcaagacg tccgtctggt cggagctggg cggcgcggtg    180
ggggacctgg gcacctacat ccccatcgtg ctggcgctgt cgctggcctc ccacctcgac    240
ctcggcacca cgctcatctt caccgcgctc tacaacttcg ccagcggcgt gctcttcggg    300
atccccatgc ccgtccagcc catgaagtcc atcgccgccg tcgcgctctc ctcggcgcac    360
ctcaccgtcc cgcagatcat gggcgcggng atcgccgtcg ccgccatcct cctcttcctc    420
```

```
ggcgccacgg ggctcatgac cgcctctac cgcgtgctcc cgctccccgt cgtccgcggc    480
gt                                                                  482
```

<210> SEQ ID NO 39
<211> LENGTH: 159
<212> TYPE: PRT
<213> ORGANISM: Hordeum vulgare
<220> FEATURE:
<221> NAME/KEY: misc_feature
<222> LOCATION: (129)..(129)
<223> OTHER INFORMATION: Xaa can be any naturally occurring amino acid

<400> SEQUENCE: 39

```
Thr His Phe Tyr Thr Gln Phe Ser Ser His Pro Gln Gln Asp Ser Ala
1               5                   10                  15

Val Val Gln Pro Ala Met Ala Ser Ser Ala Gly Asp Pro Leu Leu Pro
            20                  25                  30

Gly Glu Pro His Arg Arg Ser Phe Leu Pro Pro Ser Ile Arg Leu Lys
        35                  40                  45

Thr Ser Val Trp Ser Glu Leu Gly Gly Ala Val Gly Asp Leu Gly Thr
    50                  55                  60

Tyr Ile Pro Ile Val Leu Ala Leu Ser Leu Ala Ser His Leu Asp Leu
65                  70                  75                  80

Gly Thr Thr Leu Ile Phe Thr Ala Leu Tyr Asn Phe Ala Ser Gly Val
                85                  90                  95

Leu Phe Gly Ile Pro Met Pro Val Gln Pro Met Lys Ser Ile Ala Ala
            100                 105                 110

Val Ala Leu Ser Ser Ala His Leu Thr Val Pro Gln Ile Met Gly Ala
        115                 120                 125

Xaa Ile Ala Val Ala Ala Ile Leu Leu Phe Leu Gly Ala Thr Gly Leu
    130                 135                 140

Met Thr Arg Leu Tyr Arg Val Leu Pro Leu Pro Val Val Arg Gly
145                 150                 155
```

<210> SEQ ID NO 40
<211> LENGTH: 389
<212> TYPE: DNA
<213> ORGANISM: Hordeum vulgare
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t

<400> SEQUENCE: 40

```
atnccgtgct nccacggcgc agncgggctg gcgggccagt accggttcgg cggccggagc    60
ggggcgtccg tggtgttcct ggccatgggc aagctggtgc tggggctggt gttcggcaac   120
tcgttcgtga cgatcctggg ggagttcccc atcggcatcc tgggcgtgat gctgctcttc   180
tcgggcgtgg agctggccat ggcgtcgcgc gacatgggga gcaaggagga gtcgttcgtg   240
atgctcgtgt gcgccggagt gtcgcttacc ggctccagcg ccgcgctggg gttcatcgcc   300
```

```
ggcgtcgtgc tgcacctgct gctgcgcctc agggagatcg actccgggga gcttgtccgc    360
cggctnagag tccggcggac tgtaagcta                                      389
```

<210> SEQ ID NO 41
<211> LENGTH: 129
<212> TYPE: PRT
<213> ORGANISM: Hordeum vulgare
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid

<400> SEQUENCE: 41

Xaa Pro Cys Xaa His Gly Ala Xaa Gly Leu Ala Gly Gln Tyr Arg Phe
1               5                   10                  15

Gly Gly Arg Ser Gly Ala Ser Val Val Phe Leu Ala Met Gly Lys Leu
            20                  25                  30

Val Leu Gly Leu Val Phe Gly Asn Ser Phe Val Thr Ile Leu Gly Glu
        35                  40                  45

Phe Pro Ile Gly Ile Leu Gly Val Met Leu Leu Phe Ser Gly Val Glu
    50                  55                  60

Leu Ala Met Ala Ser Arg Asp Met Gly Ser Lys Glu Glu Ser Phe Val
65                  70                  75                  80

Met Leu Val Cys Ala Gly Val Ser Leu Thr Gly Ser Ser Ala Ala Leu
                85                  90                  95

Gly Phe Ile Ala Gly Val Val Leu His Leu Leu Leu Arg Leu Arg Glu
            100                 105                 110

Ile Asp Ser Gly Glu Leu Val Arg Arg Xaa Arg Val Arg Arg Thr Val
        115                 120                 125

Ser

<210> SEQ ID NO 42
<211> LENGTH: 778
<212> TYPE: DNA
<213> ORGANISM: Triticum aestivum

<400> SEQUENCE: 42

```
ctcggtgcca cggggctcat gacctgcctc taccgcgtcc tcccgctccc cgtcgtccgc     60
ggcgtgcagc tctcccaggg cctctccttc gccttcaccg ccgtcaagta catcccgcta    120
cgaccaggac ttctcgcgct cctcctccgc ctccacctcc gtggagcgcc cctgctcgg    180 cctcgacggc ctgctgctcg cgctcgccgc gctgctcttc atcctcctcg ccaccggcgc    240
cggggacgac gacgatgccg tcaacggagc ctacggccgc cagcgcac gccgtcgctc     300 ctgcggccgc gtcccggcgg cgctgatcgt gttcgcgctc gggctggtgc tctgcttcgt    360
gcgtgacccc tccatcttcc gcggcctccg cttcggccg gcgccactgg ggctggtgag    420
gataacatgg gacgatttca agatcgggtt ctggcaggcg gccgtgccgc agctcccgct    480
ctcggtgctc aactctgtga tcgccgtgtg caagctgtcg tccgacctgt tccgggagca    540
```

-continued

```
ggcggagctg tcgccggcga gggtgtccgt cagcgtgggg ctcatgaacc tggtggggtg      600
ctggttcggc gccatgccgt gctgccacgg cgcgggcggc ctggcggggc agtaccggtt      660
cggcggccgg agcggcgcgt ccgtggtgtt cctggccatc ggcaagctgg tgctcgggct      720
ggtgttcggc aactcgttcg tgacgattct ggggaagttt ccatcggcat actgggcg       778
```

<210> SEQ ID NO 43
<211> LENGTH: 258
<212> TYPE: PRT
<213> ORGANISM: Triticum aestivum

<400> SEQUENCE: 43

```
Ser Val Pro Arg Gly Ser Pro Ala Ser Thr Ala Ser Ser Arg Ser Pro
1               5                  10                  15

Ser Ser Ala Ala Cys Ser Ser Pro Arg Ala Ser Pro Ser Pro Ser Pro
            20                  25                  30

Pro Ser Ser Thr Ser Arg Tyr Asp Gln Asp Phe Ser Arg Ser Ser Ser
        35                  40                  45

Ala Ser Thr Ser Val Glu Arg Pro Leu Leu Gly Leu Asp Gly Leu Leu
    50                  55                  60

Leu Ala Leu Ala Ala Leu Leu Phe Ile Leu Leu Ala Thr Gly Ala Gly
65                  70                  75                  80

Asp Asp Asp Asp Ala Val Asn Gly Ala Tyr Gly Arg Ala Ser Ala Arg
                85                  90                  95

Arg Arg Ser Cys Gly Arg Val Pro Ala Ala Leu Ile Val Phe Ala Leu
            100                 105                 110

Gly Leu Val Leu Cys Phe Val Arg Asp Pro Ser Ile Phe Arg Gly Leu
        115                 120                 125

Arg Phe Gly Pro Ala Pro Leu Gly Leu Val Arg Ile Thr Trp Asp Asp
    130                 135                 140

Phe Lys Ile Gly Phe Trp Gln Ala Ala Val Pro Gln Leu Pro Leu Ser
145                 150                 155                 160

Val Leu Asn Ser Val Ile Ala Val Cys Lys Leu Ser Ser Asp Leu Phe
                165                 170                 175

Pro Glu Gln Ala Glu Leu Ser Pro Ala Arg Val Ser Val Ser Val Gly
            180                 185                 190

Leu Met Asn Leu Val Gly Cys Trp Phe Gly Ala Met Pro Cys Cys His
        195                 200                 205

Gly Ala Gly Gly Leu Ala Gly Gln Tyr Arg Phe Gly Gly Arg Ser Gly
    210                 215                 220

Ala Ser Val Val Phe Leu Ala Ile Gly Lys Leu Val Leu Gly Leu Val
225                 230                 235                 240

Phe Gly Asn Ser Phe Val Thr Ile Leu Gly Lys Phe Pro Ser Ala Tyr
                245                 250                 255

Trp Ala
```

<210> SEQ ID NO 44
<211> LENGTH: 655
<212> TYPE: DNA
<213> ORGANISM: Zea mays

<400> SEQUENCE: 44

```
tttttttttt ttttattcgg cgacccatcg attctgaggg ccttcgcttc gggccgtcgc      60
ctctacggct cgtcgggatc acctgggacg atttcaagat cggggttctgg aaggtgccg    120 tgccgcagct cccgctgtcc gtgctcaact cggtgatcgc ggtgtgcaag ctctcgtcgg    180
```

| | |
|---|---|
| atctgttccc ctatcgggcc gagctctccc cggcgcgggt gtcggtgagc gtcggcctca | 240 |
| tgaacttcgt cggctgctgg ttcggcgcca tgccgtgctg ccacggcgcg ggcggattgg | 300 |
| cggggcagta ccggttcggc ggccggagcg gcgcgtccgt ggtgttcctg gccatcggca | 360 |
| agctggcgct ggggcttgtg ttcggaaact cgttcgtgac gatcctcggc cagttcccga | 420 |
| tcgggatact gggcgtcatg ctgctcttct ccgggatcga gcttgccatg gcgtcgcgcg | 480 |
| acatgggtac taaggaggag tccttcgtca tgcttatctg cgccggagtc tcgctcacgg | 540 |
| gctcgagcgc cgcgctgggg ttcatctcgg ggattgtttt gtacctgctg ctgcgcctca | 600 |
| gggacgtgga ctaccaagca ctagccggcc gctggggctc tgaccgccgg cgaac | 655 |

<210> SEQ ID NO 45
<211> LENGTH: 217
<212> TYPE: PRT
<213> ORGANISM: Zea mays

<400> SEQUENCE: 45

Phe Phe Phe Phe Ile Arg Arg Pro Ile Asp Ser Glu Gly Leu Arg Phe
1               5                  10                  15

Gly Pro Ser Pro Leu Arg Leu Val Gly Ile Thr Trp Asp Asp Phe Lys
            20                  25                  30

Ile Gly Phe Trp Glu Gly Ala Val Pro Gln Leu Pro Leu Ser Val Leu
        35                  40                  45

Asn Ser Val Ile Ala Val Cys Lys Leu Ser Ser Asp Leu Phe Pro Tyr
    50                  55                  60

Arg Ala Glu Leu Ser Pro Ala Arg Val Ser Val Ser Val Gly Leu Met
65                  70                  75                  80

Asn Phe Val Gly Cys Trp Phe Gly Ala Met Pro Cys Cys His Gly Ala
                85                  90                  95

Gly Gly Leu Ala Gly Gln Tyr Arg Phe Gly Gly Arg Ser Gly Ala Ser
            100                 105                 110

Val Val Phe Leu Ala Ile Gly Lys Leu Ala Leu Gly Leu Val Phe Gly
        115                 120                 125

Asn Ser Phe Val Thr Ile Leu Gly Gln Phe Pro Ile Gly Ile Leu Gly
    130                 135                 140

Val Met Leu Leu Phe Ser Gly Ile Glu Leu Ala Met Ala Ser Arg Asp
145                 150                 155                 160

Met Gly Thr Lys Glu Glu Ser Phe Val Met Leu Ile Cys Ala Gly Val
                165                 170                 175

Ser Leu Thr Gly Ser Ser Ala Ala Leu Gly Phe Ile Ser Gly Ile Val
            180                 185                 190

Leu Tyr Leu Leu Leu Arg Leu Arg Asp Val Asp Tyr Gln Ala Leu Ala
        195                 200                 205

Gly Arg Trp Gly Ser Asp Arg Arg Arg
    210                 215

<210> SEQ ID NO 46
<211> LENGTH: 345
<212> TYPE: DNA
<213> ORGANISM: Medicago truncatula

<400> SEQUENCE: 46

| | |
|---|---|
| aagactcacc accatacaaa agtaaaaaaa caacttaaat ttccattcaa cattatctga | 60 |
| actcaatgga gccatgggtg accttggcac atacatacca atagtacttt cactcaccct | 120 |
| ttccaaaaac ctcaaccttg gcaccacttt gattttcacc ggcttctata acttcctcac | 180 |

```
cggtgccatg tacggtgttc ctatgccagt tcagcccatg aaatccatag ctgccgttgc      240
actctccgac ccctctttcg gtatcccgga gatcatggct tccggtatct taaccggagc      300
tgttttattg gttttgggtt ttactgggtt gatgaaattg gctta                      345
```

<210> SEQ ID NO 47
<211> LENGTH: 114
<212> TYPE: PRT
<213> ORGANISM: Medicago truncatula

<400> SEQUENCE: 47

```
Arg Leu Thr Thr Ile Gln Lys Val Lys Asn Asn Leu Asn Phe His Ser
1               5                   10                  15

Thr Leu Ser Glu Leu Asn Gly Ala Met Gly Asp Leu Gly Thr Tyr Ile
            20                  25                  30

Pro Ile Val Leu Ser Leu Thr Leu Ser Lys Asn Leu Asn Leu Gly Thr
        35                  40                  45

Thr Leu Ile Phe Thr Gly Phe Tyr Asn Phe Leu Thr Gly Ala Met Tyr
    50                  55                  60

Gly Val Pro Met Pro Val Gln Pro Met Lys Ser Ile Ala Ala Val Ala
65                  70                  75                  80

Leu Ser Asp Pro Ser Phe Gly Ile Pro Glu Ile Met Ala Ser Gly Ile
                85                  90                  95

Leu Thr Gly Ala Val Leu Leu Val Leu Gly Phe Thr Gly Leu Met Lys
            100                 105                 110

Leu Ala
```

<210> SEQ ID NO 48
<211> LENGTH: 580
<212> TYPE: DNA
<213> ORGANISM: Medicago truncatula

<400> SEQUENCE: 48

```
gcacgagatt caaagaagtg atgaaggtgg aagaaagact aagatgaata aactaagaaa       60
gattattttt tcacttcctt ctgcttttat agtctttgta ttgggaatag ttttggtttt      120
tataagaaga agtgaagttg tgcatgaaat taaatttgga ccctctaaaa tagaagtaat      180
gaaattcact aaagaaaatt ggaagaaagg ttttattaaa ggtgcaattc cacaacttcc      240
attgtcaatg ttgaactcag tgatagctgt ttgtaaatta tcaacagatc ttttccctga      300
aagggaattt tcagttacat caatttcagt gacagttgga ctaatgaatt tagttggttc      360
ttggtttggt gctgtgccaa cttgtcatgg tgctggagga ctagcaggac agtataaatt      420
tggaggaagg agtggagggt gtgttgcact tcttggtttt gcaaaattgg tattgggatt      480
ggttttagga acttctttgg cacacatttt gcaacaattt ccagttggga ttttaggtgt      540 gttactttg tttgctggta ttgaacttgc tatgtgtgct                             580
```

<210> SEQ ID NO 49
<211> LENGTH: 193
<212> TYPE: PRT
<213> ORGANISM: Medicago truncatula

<400> SEQUENCE: 49

```
His Glu Ile Gln Arg Ser Asp Glu Gly Gly Arg Lys Thr Lys Met Asn
1               5                   10                  15

Lys Leu Arg Lys Ile Ile Phe Ser Leu Pro Ser Ala Phe Ile Val Phe
            20                  25                  30
```

```
Val Leu Gly Ile Val Leu Val Phe Ile Arg Arg Ser Glu Val Val His
        35                  40                  45

Glu Ile Lys Phe Gly Pro Ser Lys Ile Glu Val Met Lys Phe Thr Lys
 50                  55                  60

Glu Asn Trp Lys Lys Gly Phe Ile Lys Gly Ala Ile Pro Gln Leu Pro
 65                  70                  75                  80

Leu Ser Met Leu Asn Ser Val Ile Ala Val Cys Lys Leu Ser Thr Asp
                 85                  90                  95

Leu Phe Pro Glu Arg Glu Phe Ser Val Thr Ser Ile Ser Val Thr Val
            100                 105                 110

Gly Leu Met Asn Leu Val Gly Ser Trp Phe Gly Ala Val Pro Thr Cys
        115                 120                 125

His Gly Ala Gly Gly Leu Ala Gly Gln Tyr Lys Phe Gly Gly Arg Ser
    130                 135                 140

Gly Gly Cys Val Ala Leu Leu Gly Phe Ala Lys Leu Val Leu Gly Leu
145                 150                 155                 160

Val Leu Gly Thr Ser Leu Ala His Ile Leu Gln Gln Phe Pro Val Gly
                165                 170                 175

Ile Leu Gly Val Leu Leu Leu Phe Ala Gly Ile Glu Leu Ala Met Cys
            180                 185                 190

Ala

<210> SEQ ID NO 50
<211> LENGTH: 34
<212> TYPE: DNA
<213> ORGANISM: Artificial Sequence
<220> FEATURE:
<223> OTHER INFORMATION: Primer: attB1 9636.m0012

<400> SEQUENCE: 50
aaaaagcagg cttaggcgag cagagaagag aaga                              34

<210> SEQ ID NO 51
<211> LENGTH: 33
<212> TYPE: DNA
<213> ORGANISM: Artificial Sequence
<220> FEATURE:
<223> OTHER INFORMATION: Primer: attB2 9636.m00012

<400> SEQUENCE: 51
agaaagctgg gtgcggaacg agctgtattg agt                               33

<210> SEQ ID NO 52
<211> LENGTH: 34
<212> TYPE: DNA
<213> ORGANISM: Artificial Sequence
<220> FEATURE:
<223> OTHER INFORMATION: Primer: attB1 m04384-ATG

<400> SEQUENCE: 52
aaaaagcagg ctatatggca tcctccgccg gcga                              34

<210> SEQ ID NO 53
<211> LENGTH: 33
<212> TYPE: DNA
<213> ORGANISM: Artificial Sequence
<220> FEATURE:
<223> OTHER INFORMATION: Primer: attB2 m04384
```

-continued

```
<400> SEQUENCE: 53
agaaagctgg gtatcaagca tctccagccc cat                                    33
```